(12) United States Patent
Buschman et al.

(10) Patent No.: US 8,888,699 B2
(45) Date of Patent: Nov. 18, 2014

(54) THERAPY USING PERTURBATION AND EFFECT OF PHYSIOLOGICAL SYSTEMS

(75) Inventors: Hendrik Peter Johan Buschman, Borne (NL); Richard N. M. Cornelussen, Maastricht (NL); Michael Roland Scott Hill, Minneapolis, MN (US); Lilian Kornet, Maastricht (NL); Simone Cornelia Maria Anna Ordelman, Enschede (NL); Petrus Hermanus Veltink, Haaksbergen (NL)

(73) Assignee: Medtronic, Inc., Minneapolis, MN (US)

( * ) Notice: Subject to any disclaimer, the term of this patent is extended or adjusted under 35 U.S.C. 154(b) by 239 days.

(21) Appl. No.: 13/094,327

(22) Filed: Apr. 26, 2011

(65) Prior Publication Data
US 2011/0270343 A1  Nov. 3, 2011

Related U.S. Application Data

(60) Provisional application No. 61/329,374, filed on Apr. 29, 2010, provisional application No. 61/417,745, filed on Nov. 29, 2010.

(51) Int. Cl.
*A61B 5/00* (2006.01)
*A61N 1/365* (2006.01)
*A61N 1/36* (2006.01)

(52) U.S. Cl.
CPC ............ *A61N 1/36114* (2013.01); *A61N 1/365* (2013.01)
USPC ............................................................ 600/300

(58) Field of Classification Search
CPC ..................... A61B 5/04–5/04018; A61B 5/05
USPC .............. 607/1, 2, 68–74; 600/544–548, 300, 600/508
See application file for complete search history.

(56) References Cited

U.S. PATENT DOCUMENTS

| 3,674,013 A | 7/1972 | Polanyl |
| 3,804,098 A | 4/1974 | Friedman |
| 3,937,226 A | 2/1976 | Funke |

(Continued)

FOREIGN PATENT DOCUMENTS

| AU | 199890156 | 3/1999 |
| AU | 779255 | 1/2001 |

(Continued)

OTHER PUBLICATIONS

US 6,184,239, 02/2001, Puskas (withdrawn).

(Continued)

*Primary Examiner* — Scott Getzow
(74) *Attorney, Agent, or Firm* — Mueting Raasch & Gebhardt, P.A.

(57) ABSTRACT

Methods for treating a patient and further to devices for performing such treatment, e.g., methods and devices to perturb at least one physiological system and deliver therapy to the patient based on the effects of such perturbation. For example, a method for using an implantable medical device is disclosed that involves a method for using an implantable medical device delivering electrical stimuli to an afferent nerve associated with the selected organ. The efferent electrical activity is monitored in an efferent nerve responsive to delivering electrical stimuli to the afferent nerve, the monitored efferent electrical activity includes an indirect component of a compound action potential (CAP). A status of the selected organ is assessed based upon the indirect component.

20 Claims, 11 Drawing Sheets

(56) References Cited

U.S. PATENT DOCUMENTS

| | | |
|---|---|---|
| 4,088,138 A | 5/1978 | Diack et al. |
| 4,088,140 A | 5/1978 | Rockland et al. |
| 4,161,952 A | 7/1979 | Kinney et al. |
| 4,176,660 A | 12/1979 | Mylrea et al. |
| 4,198,963 A | 4/1980 | Barkalow et al. |
| 4,303,075 A | 12/1981 | Heilman et al. |
| 4,304,239 A | 12/1981 | Perlin |
| 4,321,929 A | 3/1982 | Lemelson et al. |
| 4,332,259 A | 6/1982 | McCorkle, Jr. |
| 4,351,330 A | 9/1982 | Scarberry |
| 4,354,497 A | 10/1982 | Kahn |
| 4,428,378 A | 1/1984 | Anderson et al. |
| 4,458,677 A | 7/1984 | McCorkle, Jr. |
| 4,485,813 A | 12/1984 | Anderson et al. |
| 4,535,774 A | 8/1985 | Olson |
| 4,548,203 A | 10/1985 | Tacker, Jr. et al. |
| 4,574,807 A | 3/1986 | Hewson et al. |
| 4,603,705 A | 8/1986 | Speicher et al. |
| 4,640,298 A | 2/1987 | Pless et al. |
| 4,671,295 A | 6/1987 | Abrams et al. |
| 4,715,367 A | 12/1987 | Crossley |
| 4,722,347 A | 2/1988 | Abrams et al. |
| 4,750,495 A | 6/1988 | Moore et al. |
| 4,753,244 A | 6/1988 | Landymore et al. |
| 4,919,147 A | 4/1990 | Reinhardt et al. |
| 4,928,688 A | 5/1990 | Mower |
| 4,929,688 A | 5/1990 | Allen et al. |
| 4,931,464 A | 6/1990 | Grover et al. |
| 4,951,667 A | 8/1990 | Markowitz et al. |
| 4,952,586 A | 8/1990 | Morris et al. |
| 4,960,133 A | 10/1990 | Hewson |
| 4,969,463 A | 11/1990 | Dahl et al. |
| 5,003,991 A | 4/1991 | Takayama et al. |
| 5,007,893 A | 4/1991 | Row |
| 5,014,698 A | 5/1991 | Cohen |
| 5,024,228 A | 6/1991 | Goldstone et al. |
| 5,025,807 A | 6/1991 | Zabara |
| 5,036,848 A | 8/1991 | Hewson |
| 5,044,367 A | 9/1991 | Endres et al. |
| 5,050,600 A | 9/1991 | Parks |
| 5,052,390 A | 10/1991 | Hewson |
| 5,056,519 A | 10/1991 | Vince |
| 5,056,532 A | 10/1991 | Hull et al. |
| 5,117,822 A | 6/1992 | Laghi |
| 5,117,828 A | 6/1992 | Metzger et al. |
| 5,125,406 A | 6/1992 | Goldstone et al. |
| 5,127,407 A | 7/1992 | Tan |
| 5,129,392 A | 7/1992 | Bardy et al. |
| 5,154,170 A | 10/1992 | Bennett et al. |
| 5,154,172 A | 10/1992 | Terry, Jr. et al. |
| 5,156,149 A | 10/1992 | Hudrlik |
| 5,156,151 A | 10/1992 | Imran |
| 5,174,289 A | 12/1992 | Cohen |
| 5,178,149 A | 1/1993 | Imburgia et al. |
| 5,179,950 A | 1/1993 | Stanislaw |
| 5,179,952 A | 1/1993 | Buinevicius et al. |
| 5,186,170 A | 2/1993 | Varrichio et al. |
| 5,188,104 A | 2/1993 | Wernicke et al. |
| 5,199,428 A | 4/1993 | Obel et al. |
| 5,203,326 A | 4/1993 | Collins |
| 5,205,285 A | 4/1993 | Baker, Jr. |
| 5,215,086 A | 6/1993 | Terry, Jr. et al. |
| 5,231,988 A | 8/1993 | Wernicke et al. |
| 5,235,980 A | 8/1993 | Varrichio et al. |
| 5,243,980 A | 9/1993 | Mehra |
| 5,263,480 A | 11/1993 | Wernicke et al. |
| 5,265,603 A | 11/1993 | Hudrlik |
| 5,265,623 A | 11/1993 | Kroll et al. |
| 5,267,560 A | 12/1993 | Cohen |
| 5,269,298 A | 12/1993 | Adams et al. |
| 5,269,303 A | 12/1993 | Wernicke et al. |
| 5,282,468 A | 2/1994 | Klepinski |
| 5,284,146 A | 2/1994 | Czar et al. |
| 5,292,338 A | 3/1994 | Bardy |
| 5,299,569 A | 4/1994 | Wernicke et al. |
| 5,304,120 A | 4/1994 | Crandell et al. |
| 5,304,206 A | 4/1994 | Baker, Jr. et al. |
| 5,304,220 A | 4/1994 | Maginot |
| 5,306,293 A | 4/1994 | Zacouto |
| 5,315,995 A | 5/1994 | Rivers |
| 5,320,642 A | 6/1994 | Scherlag |
| 5,330,507 A | 7/1994 | Schwartz |
| 5,330,515 A | 7/1994 | Rutecki et al. |
| 5,334,221 A | 8/1994 | Bardy |
| 5,335,657 A | 8/1994 | Terry, Jr. et al. |
| 5,354,318 A | 10/1994 | Taepke |
| 5,356,425 A | 10/1994 | Bardy et al. |
| 5,365,926 A | 11/1994 | Desai |
| 5,379,765 A | 1/1995 | Kajiwara et al. |
| 5,403,356 A | 4/1995 | Hill et al. |
| 5,411,529 A | 5/1995 | Hudrlik |
| 5,411,531 A | 5/1995 | Hill et al. |
| 5,417,713 A | 5/1995 | Cohen |
| 5,423,877 A | 6/1995 | Mackey |
| 5,456,254 A | 10/1995 | Pietroski et al. |
| 5,458,625 A | 10/1995 | Kendall |
| 5,476,485 A | 12/1995 | Weinberg et al. |
| 5,501,702 A | 3/1996 | Plicchi et al. |
| 5,501,703 A | 3/1996 | Holsheimer et al. |
| 5,507,784 A | 4/1996 | Hill et al. |
| 5,514,161 A | 5/1996 | Limousin |
| 5,522,853 A | 6/1996 | Kroll |
| 5,522,854 A | 6/1996 | Ideker et al. |
| 5,531,776 A | 7/1996 | Ward et al. |
| 5,540,730 A | 7/1996 | Terry, Jr. |
| 5,540,732 A | 7/1996 | Testerman |
| 5,545,186 A | 8/1996 | Olson et al. |
| 5,549,655 A | 8/1996 | Erickson |
| 5,571,150 A | 11/1996 | Wernicke et al. |
| 5,578,061 A | 11/1996 | Stroetmann et al. |
| 5,584,867 A | 12/1996 | Limousin |
| 5,611,350 A | 3/1997 | John |
| 5,620,468 A | 4/1997 | Mongeon et al. |
| 5,632,267 A | 5/1997 | Hognelid et al. |
| 5,651,378 A | 7/1997 | Matheny et al. |
| 5,656,420 A | 8/1997 | Chien |
| 5,658,318 A | 8/1997 | Stroetmann et al. |
| 5,662,689 A | 9/1997 | Elsberry et al. |
| 5,668,117 A | 9/1997 | Shapiro |
| 5,674,259 A | 10/1997 | Gray |
| 5,683,429 A | 11/1997 | Mehra |
| 5,690,681 A | 11/1997 | Geddes et al. |
| 5,700,282 A | 12/1997 | Zabara |
| 5,707,400 A | 1/1998 | Terry, Jr. et al. |
| 5,713,924 A | 2/1998 | Min et al. |
| 5,713,929 A | 2/1998 | Hess et al. |
| 5,720,768 A | 2/1998 | Verboven-Nelissen |
| 5,755,682 A | 5/1998 | Knudson et al. |
| 5,782,874 A | 7/1998 | Loos |
| 5,791,187 A | 8/1998 | Chang |
| 5,792,187 A | 8/1998 | Adams |
| 5,792,203 A | 8/1998 | Schroeppel |
| 5,797,970 A | 8/1998 | Pouvreau |
| 5,799,661 A | 9/1998 | Boyd et al. |
| 5,824,021 A | 10/1998 | Rise |
| 5,836,994 A | 11/1998 | Bourgeois |
| 5,840,076 A | 11/1998 | Swanson et al. |
| 5,843,133 A | 12/1998 | Routh et al. |
| 5,846,263 A | 12/1998 | Peterson et al. |
| 5,846,264 A | 12/1998 | Andersson et al. |
| 5,855,592 A | 1/1999 | McGee et al. |
| 5,865,838 A | 2/1999 | Obel et al. |
| 5,874,420 A | 2/1999 | Pelleg |
| 5,876,422 A | 3/1999 | van Groeningen |
| 5,889,033 A | 3/1999 | Kaminski |
| 5,893,881 A | 4/1999 | Elsberry et al. |
| 5,893,882 A | 4/1999 | Peterson et al. |
| 5,902,324 A | 5/1999 | Thompson et al. |
| 5,913,876 A | 6/1999 | Taylor et al. |
| 5,916,239 A | 6/1999 | Geddes et al. |
| 5,928,272 A | 7/1999 | Adkins et al. |
| 5,964,789 A | 10/1999 | Karsdon |
| 5,971,911 A | 10/1999 | Wilk |
| 5,977,408 A | 11/1999 | Levin et al. |

(56) References Cited

U.S. PATENT DOCUMENTS

| | | |
|---|---|---|
| 5,978,700 A | 11/1999 | Nigam |
| 5,991,656 A | 11/1999 | Olson et al. |
| 5,995,872 A | 11/1999 | Bourgeois |
| 5,998,386 A | 12/1999 | Feldman |
| 6,006,134 A | 12/1999 | Hill et al. |
| 6,007,559 A | 12/1999 | Arkans |
| 6,014,588 A | 1/2000 | Fitz |
| 6,018,682 A | 1/2000 | Rise |
| 6,042,538 A | 3/2000 | Puskas |
| 6,043,273 A | 3/2000 | Duhaylongsod |
| 6,060,454 A | 5/2000 | Duhaylongsod |
| 6,073,048 A | 6/2000 | Kieval et al. |
| 6,087,394 A | 7/2000 | Duhaylongsod |
| 6,091,988 A | 7/2000 | Warman et al. |
| 6,101,412 A | 8/2000 | Duhaylongsod |
| 6,103,722 A | 8/2000 | Schultz et al. |
| 6,127,410 A | 10/2000 | Duhaylongsod |
| 6,134,470 A | 10/2000 | Hartlaub |
| 6,141,589 A | 10/2000 | Duhaylongsod |
| 6,141,590 A | 10/2000 | Renirie et al. |
| 6,167,305 A | 12/2000 | Cammilli et al. |
| 6,185,459 B1 | 2/2001 | Mehra et al. |
| 6,221,851 B1 | 4/2001 | Feldman |
| 6,234,985 B1 | 5/2001 | Lurie et al. |
| 6,253,108 B1 | 6/2001 | Rosborough et al. |
| 6,256,537 B1 | 7/2001 | Stoop et al. |
| 6,259,947 B1 | 7/2001 | Olson et al. |
| 6,266,564 B1 | 7/2001 | Hill et al. |
| 6,272,380 B1 | 8/2001 | Warman et al. |
| 6,299,564 B1 | 10/2001 | Gessler et al. |
| 6,303,293 B1 | 10/2001 | Patterson et al. |
| 6,304,777 B1 | 10/2001 | Ben-Haim et al. |
| 6,381,499 B1 | 4/2002 | Taylor et al. |
| 6,393,316 B1 | 5/2002 | Gillberg et al. |
| 6,414,018 B1 | 7/2002 | Duhaylongsod |
| 6,429,217 B1 | 8/2002 | Puskas |
| 6,438,421 B1 | 8/2002 | Stahmann et al. |
| 6,442,429 B1 | 8/2002 | Hill et al. |
| 6,449,507 B1 | 9/2002 | Hill et al. |
| 6,473,644 B1 | 10/2002 | Terry, Jr. et al. |
| 6,479,523 B1 | 11/2002 | Puskas |
| 6,487,446 B1 | 11/2002 | Hill et al. |
| 6,532,388 B1 | 3/2003 | Hill et al. |
| 6,537,540 B1 | 3/2003 | Burstein et al. |
| 6,542,774 B2 | 4/2003 | Hill et al. |
| 6,554,781 B1 | 4/2003 | Carter et al. |
| 6,572,895 B2 | 6/2003 | Smith et al. |
| 6,587,719 B1 | 7/2003 | Barrett et al. |
| 6,609,025 B2 | 8/2003 | Barrett et al. |
| 6,611,713 B2 | 8/2003 | Schauerte |
| 6,622,038 B2 | 9/2003 | Barrett et al. |
| 6,622,041 B2 | 9/2003 | Terry, Jr. et al. |
| 6,622,047 B2 | 9/2003 | Barrett et al. |
| 6,628,987 B1 | 9/2003 | Hill et al. |
| 6,656,960 B2 | 12/2003 | Puskas |
| 6,690,973 B2 | 2/2004 | Hill et al. |
| 6,711,436 B1 | 3/2004 | Duhaylongsod |
| 6,718,208 B2 | 4/2004 | Hill et al. |
| 6,721,603 B2 | 4/2004 | Zabara et al. |
| 6,731,978 B2 | 5/2004 | Olson et al. |
| 6,735,471 B2 | 5/2004 | Hill et al. |
| 6,738,667 B2 | 5/2004 | Deno et al. |
| 6,778,854 B2 | 8/2004 | Puskas |
| RE38,654 E | 11/2004 | Hill et al. |
| RE38,705 E | 2/2005 | Hill et al. |
| 6,850,801 B2 | 2/2005 | Kieval et al. |
| 6,889,077 B2 | 5/2005 | Bornzin et al. |
| 6,904,318 B2 | 6/2005 | Hill et al. |
| 6,912,419 B2 | 6/2005 | Hill et al. |
| 7,024,238 B2 * | 4/2006 | Bergethon .................. 600/544 |
| 7,138,607 B2 | 11/2006 | Wang et al. |
| 7,139,607 B1 | 11/2006 | Shelchuk |
| 7,200,438 B2 | 4/2007 | Euler |
| 7,225,019 B2 | 5/2007 | Jahns et al. |
| 7,231,254 B2 | 6/2007 | DiLorenzo |
| 7,245,967 B1 | 7/2007 | Shelchuk |
| 7,269,457 B2 | 9/2007 | Shafer et al. |
| 7,299,091 B2 | 11/2007 | Barrett et al. |
| 7,321,793 B2 | 1/2008 | Ben Ezra et al. |
| 7,493,161 B2 | 2/2009 | Libbus et al. |
| 7,499,748 B2 | 3/2009 | Moffitt et al. |
| 7,509,166 B2 | 3/2009 | Libbus |
| 7,542,800 B2 | 6/2009 | Libbus et al. |
| 7,548,780 B2 | 6/2009 | Libbus et al. |
| 7,555,341 B2 | 6/2009 | Moffitt et al. |
| 7,555,345 B2 | 6/2009 | Wahlstrand et al. |
| 7,587,238 B2 | 9/2009 | Moffit et al. |
| 7,643,875 B2 | 1/2010 | Heil, Jr. et al. |
| 7,711,421 B2 | 5/2010 | Shafer et al. |
| 7,826,899 B1 | 11/2010 | Ryu et al. |
| 7,840,278 B1 | 11/2010 | Puskas |
| 8,012,189 B1 | 9/2011 | Webb et al. |
| 8,032,215 B2 | 10/2011 | Libbus et al. |
| 8,036,741 B2 | 10/2011 | Jahns et al. |
| 8,036,756 B2 | 10/2011 | Swoyer et al. |
| 2001/0049543 A1 | 12/2001 | Kroll |
| 2002/0035335 A1 | 3/2002 | Schauerte |
| 2002/0049478 A1 | 4/2002 | Ding et al. |
| 2002/0072782 A1 | 6/2002 | Osorio et al. |
| 2002/0107553 A1 | 8/2002 | Hill et al. |
| 2002/0198570 A1 | 12/2002 | Puskas |
| 2002/0198571 A1 | 12/2002 | Puskas |
| 2003/0045909 A1 | 3/2003 | Gross et al. |
| 2003/0060857 A1 | 3/2003 | Perrson et al. |
| 2003/0074039 A1 | 4/2003 | Puskas |
| 2003/0187479 A1 | 10/2003 | Thong |
| 2003/0216775 A1 | 11/2003 | Hill et al. |
| 2003/0216790 A1 | 11/2003 | Hill et al. |
| 2004/0024422 A1 | 2/2004 | Hill et al. |
| 2004/0059383 A1 | 3/2004 | Puskas |
| 2004/0111118 A1 | 6/2004 | Hill et al. |
| 2004/0162584 A1 | 8/2004 | Hill et al. |
| 2004/0172075 A1 | 9/2004 | Shafer et al. |
| 2004/0186517 A1 | 9/2004 | Hill et al. |
| 2004/0186531 A1 | 9/2004 | Jahns et al. |
| 2004/0199209 A1 | 10/2004 | Hill et al. |
| 2004/0210261 A1 | 10/2004 | King et al. |
| 2005/0096707 A1 | 5/2005 | Hill et al. |
| 2005/0119704 A1 | 6/2005 | Peters et al. |
| 2005/0143412 A1 | 6/2005 | Puskas |
| 2005/0197675 A1 | 9/2005 | David et al. |
| 2006/0074450 A1 | 4/2006 | Boveja et al. |
| 2006/0095081 A1 | 5/2006 | Zhou et al. |
| 2006/0106429 A1 | 5/2006 | Libbus et al. |
| 2006/0135998 A1 | 6/2006 | Libbus et al. |
| 2006/0173494 A1 | 8/2006 | Armstrong et al. |
| 2006/0206158 A1 | 9/2006 | Wu et al. |
| 2006/0206159 A1 | 9/2006 | Moffitt et al. |
| 2006/0224202 A1 | 10/2006 | Moffitt et al. |
| 2006/0271115 A1 | 11/2006 | Ben-Ezra et al. |
| 2006/0293712 A1 | 12/2006 | Kieval et al. |
| 2007/0021792 A1 | 1/2007 | Kieval et al. |
| 2007/0021796 A1 | 1/2007 | Kieval et al. |
| 2007/0021799 A1 | 1/2007 | Kieval et al. |
| 2007/0083242 A1 | 4/2007 | Mazgalev et al. |
| 2007/0106337 A1 | 5/2007 | Errico et al. |
| 2007/0129764 A1 | 6/2007 | Burnes |
| 2007/0260283 A1 | 11/2007 | Li |
| 2007/0299476 A1 | 12/2007 | Park et al. |
| 2008/0058874 A1 | 3/2008 | Westlund et al. |
| 2008/0091240 A1 | 4/2008 | Ben-David et al. |
| 2008/0234780 A1 | 9/2008 | Smith et al. |
| 2008/0269819 A1 | 10/2008 | Zhou |
| 2008/0300640 A1 | 12/2008 | Mazgalev et al. |
| 2009/0005845 A1 | 1/2009 | David et al. |
| 2009/0234408 A1 | 9/2009 | Moffitt et al. |
| 2010/0036447 A1 | 2/2010 | Zhang et al. |
| 2010/0114208 A1 | 5/2010 | Donofrio et al. |
| 2011/0004262 A1 | 1/2011 | Bianchi et al. |
| 2011/0270332 A1 | 11/2011 | Buschman et al. |
| 2011/0270342 A1 | 11/2011 | Buschman et al. |
| 2012/0029586 A1 | 2/2012 | Kumar et al. |
| 2012/0029587 A1 | 2/2012 | Zhou et al. |
| 2012/0029600 A1 | 2/2012 | Zhou et al. |

(56) References Cited

U.S. PATENT DOCUMENTS

| | | |
|---|---|---|
| 2012/0078132 A1 | 3/2012 | Zdeblick et al. |
| 2012/0185007 A1 | 7/2012 | Ziegler et al. |
| 2012/0185008 A1 | 7/2012 | Zhou et al. |
| 2012/0185009 A1 | 7/2012 | Kornet et al. |
| 2012/0185010 A1 | 7/2012 | Zhou et al. |
| 2012/0185011 A1 | 7/2012 | Cornelussen et al. |

FOREIGN PATENT DOCUMENTS

| | | |
|---|---|---|
| CA | 2310183 | 8/1998 |
| CA | 2 376 903 A1 | 1/2001 |
| DE | 2811325 | 9/1979 |
| EP | 0440111 A2 | 8/1991 |
| EP | 0547734 A2 | 6/1993 |
| EP | 0562408 A1 | 9/1993 |
| EP | 0589252 A2 | 3/1994 |
| EP | 1 051 168 | 2/1999 |
| EP | 0756507 B1 | 2/1999 |
| EP | 1181947 A2 | 2/2002 |
| EP | 1426078 A1 | 6/2004 |
| EP | 1 005 337 B1 | 5/2005 |
| EP | 1 051 168 B1 | 3/2006 |
| EP | 1870129 A1 | 12/2007 |
| JP | 2000507363 | 8/1998 |
| JP | 2001505980 | 6/2000 |
| MX | PA00002043 | 3/2004 |
| WO | WO 92/11064 A1 | 7/1992 |
| WO | WO 97/40885 A1 | 2/1997 |
| WO | WO 97/13550 A1 | 4/1997 |
| WO | WO 99/09973 A1 | 8/1998 |
| WO | WO 99/00057 A1 | 1/1999 |
| WO | WO 99/07354 A2 | 2/1999 |
| WO | 1 005 337 | 3/1999 |
| WO | WO 99/09971 A1 | 3/1999 |
| WO | WO 99/63926 A2 | 12/1999 |
| WO | WO 00/01306 A1 | 1/2000 |
| WO | WO 00/09206 A1 | 2/2000 |
| WO | WO 01/00273 A1 | 2/2001 |
| WO | WO 01/89526 A1 | 11/2001 |
| WO | WO 02/26320 A1 | 4/2002 |
| WO | WO 03/103484 A2 | 12/2003 |
| WO | WO 03/103484 A3 | 4/2004 |
| WO | WO 2007/142563 A1 | 12/2007 |
| WO | WO 2008/144125 A1 | 11/2008 |

OTHER PUBLICATIONS

U.S. Appl. No. 12/848,010, filed Jul. 30, 2010, Zhou et al.
U.S. Appl. No. 12/848,019, filed Jul. 30, 2010, Zhou et al.
Bianchi et al., "Endocardial Transcatheter Stimulation of the AV Node Fat Pad: Stabilization of Rapid Ventricular Rate Response During Atrial Fibrillation in Left Ventricular Failure" *Journal of Cardiovascular Electrophysiology*, Jan. 2009; 20(1):103-105. Epub Jul. 3, 2008.
Bilgutay et al. "Vagal Tuning—A New Concept in the Treatment of Supraventricular Arrhythmias, Angina Pectoris, and Heart Failure," Jul. 1968, *Journal of Thoracic and Cardiovascular Surgery*, vol. 56, No. 1, pp. 71-82.
Chiou, "Efferent Vagal Innervation of the Canine Atria and Sinus and Atrioventricular Nodes: The Third Fat Pad" *Circulation*, 1997; 95:2573-2584.
Donaldson et al., "Velocity-selective recording using multi-electrode nerve cuffs," 7th Annual Conference of the International Functional Electrical Stimulation Society (IFESS), Ljubijana, Slovenia, Jun. 25-29, 2002; 5 pgs.
Eckberg, "The Human Respiratory Gate" *J. Physiol.*, 2003; 548. 2:339-352.
Laperche et al., "Potential Interests of Heart Rate Lowering Drugs" *Heart*, 1999; 81:336-341.
Ordelman et al., "Average Reference Recording from the Vagal Nerve Reveals an Evoked Indirect Response" Proceedings of the 4th International IEEE EMBS Conference on Neural Engineering Antalya, Turkey, Apr. 29-May 2, 2009.
Ordelman et al., "An Evoked Indirect Response in the Cervical Vagal Nerve" 4th Annual Symposium of the IEEE-IMBS Benelux Chapter, Nov. 9-10, 2009, Enschede, The Netherlands; p. 28.
Ordelman et al., "An Indirect Component in the Evoked Compound Action Potential of the Vagal Nerve" *J. Neural. Eng.*, 2010; 7:1-9.
Ricci et al., "Efficacy of a Dual Chamber Defibrillator with Atrial Antitachycardia Functions in Treating Spontaneous Atrial Tachyarrhythmias in Patients with Life-Threatening Ventricular Tachyarrhythmias" *European Heart Journal*, 2002; 23:1471-1479.
Rieger et al., "Experimental determination of compound action potential direction and propagation velocity from multi-electrode nerve cuffs" *Medical Engineering & Physics*, 2004; 26: 531-534.
Rossi et al., "Post-Operative Atrial Fibrillation Management by Selective Epicardial Vagal Fat Pad Stimulation" *J. Interv. Card. Electrophysiol.*, 2009; 24:37-45.
Rossi et al., "Vagal Tone Augmentation to the Atrioventricular Node in Humans: Efficacy and Safety of Burst Endocardial Stimulation" *Heart Rhythm*, May 2010; 7(5):683-689.
Zhang et al., "Optimal Ventricular Rate Slowing During Atrial Fibrillation by Feedback AV Nodal-Selective Vagal Stimulation" *Am. J. Physiol. Heart Circ. Physiol.*, 2002; 282:H1102-H1110.
Zhang et al., "Achieving Regular Slow Rhythm During Atrial Fibrillation Without Atrioventricular Nodal Ablation: Selective Vagal Stimulation Plus Ventricular Pacing" *Heart Rhythm*, 2004; 1(4):469-475.
International Search Report, PCT/US/2008/059723, Aug. 27, 2008, 6 pgs.
Written Opinion, PCT/US/2008/059723, Aug. 27, 2008, 7 pgs.
International Preliminary Report on Patentability, PCT/US/2008/059723, Oct. 27, 2009, 8 pgs.
International Search Report and Written Opinion, PCT/EP2010/003956, dated Nov. 4, 2010, 11 pgs.
Reply to Written Opinion, PCT/EP2010/003956 (WO 2011/000558) dated May 2, 2011, 4 pgs.
International Preliminary Report on Patentability, PCT/EP2010/003956, dated Jul. 20, 2011, 10 pgs.
Office Action for U.S. Appl. No. 11/740,565, mailed Dec. 30, 2009, 8 pages.
Responsive Amendment to Office Action for U.S. Appl. No. 11/740,565, filed Apr. 29, 2010, 11 pages.
Final Office Action for U.S. Appl. No. 11/740,565, mailed Jan. 21, 2011, 9 pages.
Responsive Amendment to Office Action for U.S. Appl. No. 11/740,565, filed Mar. 21, 2011, 8 pages.
Adams, "Gains in Pain Research: Past Failures Push Investigators to be More Innovative in their Treatment Approaches," *The Scientist*, Dec. 15, 2003; 17(24); 6 pages.
Agnew et al., "Considerations for Safety with Chronically Implanted Nerve Electrodes," *Epilepsia*, 1990; 31(Suppl. 2):S27-S32.
Ando et al., "Efferent Vagal Nerve Stimulation Protects Heart Against Ischemia-Induced Arrhythmias by Preserving Connexin43 Protein," *Circulation*, 2005; 112:164-470.
Annegers et al., "Epilepsy, Vagal Nerve Stimulation by the NCP System, All-Cause Mortality, and Sudden, Unexpected, Unexplained Death," *Epilepsia*, 2000; 41(5):549-553.
"Atrial Fibrillation: Current Understandings and Research Imperatives," The National Heart, Lung, and Blood Institute Working Group on Atrial Fibrillation, *JACC*, Dec. 1993; 22(7):1830-1834.
Barwell et al., "The NIM-2 Nerve Integrity Monitor in Thyroid and Parathyroid Surgery," *British Journal of Surgery*, 1997; 84:854.
Beekwilder et al., "Overview of the Clinical Applications of Vagus Nerve Stimulation," *Journal of Clinical Neurophysiology*, Apr. 2010; 27(2):130-138.
Bell et al., "Intropic Response of the Left Ventricle to Changes in Heart Rate in Anesthetized Rabbits," *Can.J. Physiol. Pharmacol.*, 1987; 65(2):179-184.
Bennetti et al., "Use of Thoracoscopy and a Minimal Thoracotomy, in Mammary-Coronary Bypass to Left Anterior Descending Artery, Without Extracorporeal Circulation," *J. Cardiovasc. Surg.*, Apr. 1995; 36(2):159-161.
Bennetti, "Direct Coronary Surgery with Saphenous Vein Bypass Without Either Cardiopulmonary Bypass or Cardiac Arrest," *J. Cardiovasc. Surg.*, 1985; 26:217-222.

(56) References Cited

OTHER PUBLICATIONS

Ben-Menachem et al., "Vagus Nerve Stimulation for Treatment of Partial Seizures: 1. A Controlled Study of Effect on Seizures," *Epilepsia*, 1994; 35(3):616-626.
Besedovsky et al., "Immunoregulatory Feedback Between Interleukin-1 and Glucocorticoid Hormones," *Science*, Aug. 8, 1986; 233(4764):652-654.
Binks et al., "High Strength Stimulation of the Vagus Nerve in Awake Humans: a Lack of Cardiorespiratory Effects," *Respiration Physiology*, 2001; 127:125-133.
Bluemel et al., "Parasympathetic Postganglionic Pathways to the Sinoatrial Node," *Am. J. Physiol.*, 1990; 259(5 Pt 2):H1504-H1510.
Borovikova et al., "Role of Vagus Nerve Signaling in CNI-1493-Mediated Suppression of Acute Inflammation," *Autonomic Neuroscience: Basic and Clinical*, 2000; 85:141-147.
Borovikova et al., "Vagus Nerve Stimulation Attenuates the Systemic Inflammatory Response to Endotoxin," *Nature*, 2000; 405(6785):458-462.
Braunwald et al., "Carotid Sinus Nerve Stimulation in the Treatment of Angina Pectoris and Supraventricular Tachycardia," *California Medicine: The Western Journal of Medicine*, 1970; 112(3):41-50.
Bristow, "The Adrenergic Nervous System in Heart Failure," *The New Eng. J. of Med.*, Sep. 27, 1984; 311(13):850-851.
Brodde et al., "Cardiac Muscarinic Receptors Decrease with Age: In Vitro and In Vivo Studies," *Journal of Clinical Investigations*, Jan. 1998; 101(2):471-478.
Bufkin et al., "Controlled Intermittent Asystole: Parmacologic Potentiation of Vagal-Induced Asystole," *Ann.Thorac. Surg.*, 1998; 66:1185-1190.
Buschman et al., "Control of Heart Rate with Vagus Nerve Stimulation," 7$^{th}$ Annual Conference of the International Functional Electrical Stimulation Society (IFESS), Ljubijana, Slovenia, Jun. 25-29, 2002. Abstract not available.
Buschman et al., "Heart Rate Control Via Vagus Nerve Stimulation," *Neuromodulation*, Jul. 2006; 9(3):214-220.
Carlson et al., "Selective Stimulation of Parasympathetic Nerve Fibers to the Human Sinoatrial Node," *Circulation*, Apr. 1992; 85(4):1311-1317.
Carlsson et al., "Therapy of Atrial Fibrillation: Rhythm Control Versus Rate Control," *PACE*, May 2000; 23:891-903.
Clarke et al., Cognitive Motor Function After Electrical Stimulation of the Vagus Nerve, *PACE*, Oct. 1992; 15(10 PartII):1603-1607.
Clarke et al., "Acute Effects of High Frequency Vagal Nerve Stimulation on Balance and Cognitive Motor Performance in Epilepsy: Three Case Study Reports," *PACE*, Oct. 1992; 15(10 PartII):1608-1613.
Clarke et al., "Electrostimulation Effects of the Vagus Nerve on Balance in Epilepsy," *PACE*, Oct. 1992; 15(10 PartII):1614-1630.
Cooper et al., "Neural Effects on Sinus Rate and Atrioventricular Conduction Produced by Electrical Stimulation from a Transvenous Electrode Catheter in the Canine Right Pulmonary Artery," *Circulation Research*, Jan. 1980; 46(1):48-57.
Daubert et al., "Inappropiate Implantable Cardioverter-Defibrillator Shocks in MADIT II: Frequency, Mechanisms, Predictors, and Survival Impact," *J. Am. Coll. Cardiol.*, 2008; 51:1357-1365.
DiMarco et al., "Adenosine: Electrophysiologic Effects and Therapeutic Use for Terminating Paroxysmal Supraventricular Tachycardia," *Circulation*, Dec. 1983; 68(6):1254-1263.
Dipiro et al., Editor, "Pharmacotherapy: A Pathophysiologic Approach," 1989; 153-157.
Diwan et al., "Inflammatory Mediators and the Failing Heart: A Translational Approach," *Cur. Mol. Med.*, 2003; 3(2):161-182.
Duhaylongsod et al., "Controlled Ventricular Asystole with Surgeon-Actuated Pacing for Off-Pump Coronary Artery Bypass Grafting: A Proposed Surgical Method," Presentation Summary, Presented at International Society for Minimally Invasive Cardiac Surgery Annual Meeting, Jun. 25, 1998, Minneapolis, MN, 1 page.
Espinosa et al., "Revision and Removal of Stimulating Electrodes Following Long-Term Therapy with the Vagus Nerve Stimulator," *Surgical Neurology*, 1999; 51: 659-664.

Fanning et al., "Reoperative Coronary Artery Bypass Grafting Without Cardiopulmonary Bypass," *Ann. Thorac. Surg.*, Feb. 1993; 55(2):486-489.
Finkel et al., "Negative Inotropic Effects of Cytokines on the Heart Mediated by Nitric Oxide," *Science*, Jul. 17, 1992; 257(5068):387-389.
Fleshner et al., "Thermogenic and Corticosterone Responses to Intravenous Cytokines (IL-1$\beta$ and TNF-$\alpha$) are Attenuated by Subdiaphragmatic Vagotomy," *J. of Neuroimmunology*, 1998; 86:134-141.
Freilich et al., "Adenosine and its Cardiovascular Effects," *American Heart Journal*, May 1992; 123(5):1324-1328.
Garcia-Perez et al., "Effect of Stimulating Non-myelinated Vagal Axons on Atrio-ventricular Conduction and Left Ventricular Function in Anaesthetized Rabbits," *Autonomic Neuroscience: Basic and Clinical*, 2001; 86:183-191.
Garnett et al., "Regional Cerebral Blood Flow in Man Manipulated by Direct Vagal Stimulation," *PACE*, Oct. 1992; 15(10 PartII):1579-1580.
Gaykema et al., "Subdiaphragmatic Vagotomy Suppresses Endotoxin-Induced Activation of Hypothalamic Corticotropin-Releasing Hormone Neurons and ACTH Secretion," *Endocrinology*, Oct. 1995; 136(10):4717-4720.
George et al., "Vagus Nerve Stimulation for Treatment of Partial Seizures: 3. Long-Term Follow-Up on First 67 Patients Exiting a Controlled Study," *Epilepsia*, 1994; 35(3):637-643.
Gorman et al., "How New Heart-Scanning Technology Could Save Your Life," *Time*, Sep. 5, 2005; 8 pages.
Guarini et al., "Efferent Vagal Fibre Stimulation Blunts Nuclear Factor-kB Activation and Protects Against Hypovolemic Hemorrhagic Shock," *Circulation*, Mar. 4, 2003; 107(8):1189-1194.
Gulick et al., "Interleukin 1 and Tumor Necrosis Factor Inhibit Cardiac Myocyte $\beta$-adrenergic Responsiveness," *Proc. Natl. Acad. Sci. USA*, Sep. 1989; 86(17):6753-6757.
Gupta, "Suppression of Paroxysmal Atrial Fibrillation by Pacing," *Indian Pacing and Electrophysiology Journal*, 2003; 3(2):45-46.
Hageman et al., "Direct and Reflex Cardiac Bradydysrhythmias From Small Vagal Nerve Stimulations," *Am. Heart J.*, Mar. 1975; 89(3):338-348 (Abstract only).
Hammond et al., "Vagus Nerve Stimulation in Humans: Neurophysiological Studies and Electrophysiological Monitoring," *Epilepsia*, 1990; 31(Suppl. 2):S51-S59.
Harvey et al., "Radiofrequency Catheter Ablation for Atrial Fibrillation," *Coronary Artery Disease*, 1995; 6:115-120.
Henning et al., "Vagal Nerve Stimulation Increases Right Ventricular Contraction and Relaxation and Heart Rate," *Cardiovascular Research*, 1996; 32:846-853.
Hirota et al., "Loss of gp130 Cardiac Muscle Cell Survival Pathway is a Critical Event in the Onset of Heart Failure during Biomechanical Stress," *Cell*, 1999; 97:189-198.
Holder et al., "Treatment of Refractory Partial Seizures: Preliminary Results of a Controlled Study," *PACE*, Oct. 1992; 15(10 PartII):1557-1571.
Israel et al., "Atrial Pacing in the Prevention of Paroxysmal Atrial Fibrillation: First Results of a New Combined Algorithm," *PACE*, Nov. 2000, Part II; 23:1888-1890.
Jalife et al., "Desensitization of the Cholinergic Receptor at the Sinoatrial Cell of the Kitten," *Am. J. Physiol.*, 1980; 238(4):H439-448.
Jones, "Vagal Control of the Rat Heart," *Exp. Physiol.*, Nov. 2001; 86(6):797-801.
Kale et al., "Atrial Septal Pacing in the Prevention of Paroxysmal Atrial Fibrillation Refractory to Antiarrhythmic Drugs," *International Journal of Cardiology*, 2002; 82:167-175.
Kamath et al., "Neurocardiac Responses to Vagoafferent Electrostimulation in Humans," *PACE*, Oct. 1992; 15(10 PartII):1581-1587.
Kandel et al., editors, Principles of Neural Science, Fourth Edition, McGraw-Hill, New York, 2000. Title page, copyright page and table of contents, 29 pgs.
Khanna et al., "Coronary Artery Surgery with Induced Temporary Asystole and Intermittent Ventricular Pacing: An Experimental Study," *Cardiovascular Surgery*, Apr. 1996, 4(2):231-236.

(56) References Cited

OTHER PUBLICATIONS

Klassen et al., "Coronary Venous Pressure and Flow: Effects of Vagal Stimulation, Aortic Occlusion and Vasodialators," Can. J. Physiol. Pharmacol., May 1984; 62(5):531,538.

Kornet et al., "Stimulation of the Intra-Cardiac Vagal Nerves Innervating the AV-Node to Control Ventricular Rate During AF: Specificity, Parameter Optimization and Chronic Use up to 3 Months," J. Interv. Card. Electrophysiol., Jan. 2012; 33(1):7-18. Published online Oct. 4, 2011.

Krown et al., "Tumor Necrosis Factor Alpha-Induced Apoptosis in Cardiac Myocytes: Involvement of the Sphingolipid Signaling Cascade in Cardiac Cell Death," J. Clin. Invest., 1996; 98(12):2854-2865.

Lagi et al., "Age-Related Changes of Cardiac Parasympathetic Modulation After Vasovagal Syncope," American Journal of Cardiology, Mar. 15, 1999; 83:977-980.

Levine et al., "Pacing for the Suppression of Paroxysmal Atrial Fibrillation in an 87-year-old Patient," Indian Pacing and Electrophysiology Journal, 2003; 3(2):88-90.

Levy et al., "Autonomic Control of Cardiac Pacemaker Activity and Atrioventricular Transmission," Journal of Applied Physiology, Oct. 1969; 27(4):465-470.

Levy et al., "Parasympathetic Control of the Heart," Chapter 4, Nervous Control of Cardiovascular Function, Oxford University Press, New York, 1984, pp. 68-94.

Li et al., "Myocardial Extracellular Matrix Remodeling in Transgenic Mice Overexpressing Tumor Necrosis Factor α can be modulated by Anti-Tumor Necrosis Factor α Therapy," PNAS, Nov. 7, 2000; 97(23):12746-12751.

Li et al, "Vagal Nerve Stimulation Markedly Improves Long-Term Survival after Chronic Heart Failure in Rats," Circulation, 2004; 109:120-124.

Lisman et al., "The Role of Tumor Necrosis Factor Alpha Blockade in the Treatment of Congestive Heart Failure," CHF, Sep./Oct. 2002; pp. 275-279.

Lockard et al., "Feasibility and Safety of Vagal Stimulation in Monkey Model," Epilepsia, 1990; 31(Supp. 2):S20-S26.

Loeb et al., "Sensitivity Differences of SA and AV Node to Vagal Stimulation: Attenuation of Vagal Effects at SA Node," Am. J. Physiol., Nov. 1981; 241(5):H684-H690.

McGregor et al., "Proteomics of Heart Disease," Human Molecular Genetics, Oct. 15, 2003; 12(Review Issue 2):R135-R144.

Maloney et al., "A New Method for Intraoperative Recurrent Laryngeal Nerve Monitoring," ENT Journal, 1994; 73(1):30-33.

Mann et al., "New Therapeutics for Chronic Heart Failure," Annu. Rev. Med., 2002; 53:59-74.

Mann, "Mechanisms and models in Heart Failure—A Combinatorial Approach," Circulation, Aug. 31, 1999; 100(9):999-1008.

Martin et al., "Fade of Cardiac Responses During Tonic Vagal Stimulation," Am. J. Physiol., 1982; 243(2):H219-H225.

Matheny et al., "Vagus Nerve Stimulation as a Method to Temporarily Slow or Arrest the Heart," Presented at the Second Utrecht MICABG Workshop, Oct. 4-5, 1996, Utrecht, Netherlands. Transcription of Presentation. Annals of Thoracic Surgery, Jun. 6, 1997; 63(6):S28-S29.

Matheny, "Techniques of Stabilization," Experiences in Minimally Invasive Surgery Conference, Jun. 19-21, 1997, Minneapolis, MN. Transcription of Presentation, 6 pages.

Mitchell, "The Role of Pacemaker and Defibrillator Therapy for the Treatment of Atrial Fibrillation," Minerva Cardioangiologica, Apr. 2004, 52(2):141-153.

Mohiuddin et al., "Safety of different Dosages of Intravenous Adenosine Used in Conjunction with Diagnostic Myocardial Imaging Techniques," Pharmacotherapy, Sep./Oct. 1993; 13(5):476-480.

Murgatroyd, "Pills and Pulses: Hybrid Therapy for Atrial Fibrillation," Journal of Cardiovascular Electrophysiology, Jan. 2002; 13(1) Suppl:S40-S46.

Nanthakumar et al, "Inappropriate Therapy from Atrial Fibrillation and Sinus Tachycardia in Automated Implantable Cardioverter Defibrillators," American Heart Journal, May 2000; 139(5):797-803.

Naritoku et al., "Chronic Vagus Nerve Stimulation Increases the Latency of the Thalamocortical Somatosensory Evoked Potential," PACE, Oct. 1992; 15(10 PartII):1572-1578.

Nerheim et al., "Heart Failure and Sudden Death in Patients with Tachycardia-Induced Cardiomyopathy and Recurrent Tachycardia," Circulation, 2004; 110:247-252.

Nobrega et al., "Resting and Reflex Heart Rate Responses During Cholinergic Stimulation with Pyridostigmine in Humans," Braz. J. Med. Biol. Res., Nov. 1996; 29(11):1461-1465 (Abstract Only).

Noonan, "And the Beat Goes on," Newsweek, Jul. 11, 2005, pp. 56-57.

Nunain et al., "Limitations and Late Complications of Third-Generation Automatic Cardioverter-Defibrillators," Circulation, 1995; 91:2204-2213.

Ogawa et al., "Acute Effects of Different Atrial Pacing Sites in Patients with Atrial Fibrillation: Comparison of Single Site and Biatrial Pacing," PACE, Oct. 2001; 24:1470-1478.

Okazawa et al., "Effect of Vagal Stimulations and Parenteral Acetylcholine on Canine Trachealis Muscle Shortening," J. Appl. Physiol., 1992; 75(6):2463-2468, (Abstract Only).

Ousdigian et al., "Continuous ICD Diagnostics Triage Patients for Urgent Intervention: Low vs. High Risk of Inappropriate Shocks for AF," Heart Rhythm Society Congress 2008, 29th Annual Scientific Sessions, May 14-17, 2008, San Francisco, CA.

Pavlov et al., "Central Muscarinic Cholinergic Regulation of the Systemic Inflammatory Response during Endotoxemia," PNAS, Mar. 28, 2006; 103(13):5219-5223.

Penry et al., "Prevention of Intractable Partial Seizures by Intermittent Vagal Stimulation in Humans: Preliminary Results," Epilepsia, 1990; 31(Suppl.2):S40-S43.

Pfister et al., "Coronary Artery Bypass Without Cardiopulmonary Bypass," Ann. Thorac. Surg., Dec. 1992; 54(6):1085-1092.

Poller et al., "Age-Dependent Changes in Cardiac Muscarinic Receptor Function in Healthy Volunteers," Journal of American College of Cardiology, Jan. 1997; 29(1):187-193.

Poole et al., "Prognostic Importance of Defibrillator Shocks in Patients with Heart Failure," New England Journal of Medicine, Sep. 4, 2008, 359:1009-1017.

Puglisi et al., "Persistent Atrial Fibrillation Worsens Heart Rate Variability, Activity and Heart Rate, as Shown by a Continuous Monitoring by Implantable Biventricular Pacemakers in Heart Failure Patients," Journal of Cardiovascular Electrophysiology, Jul. 2008; 19(7):693-701.

Pulkki, "Cytokines and Cardiomyocyte Death," Annals of Medicine, 1997; 29:339-343.

Purefellner et al., "Accuracy of Atrial Tachyarrhythmia Detection in Implantable Devices with Arrhythmia Therapies," PACE, Jul. 2004; 27:983-992.

Puskas, Declaration/Clarification of John D. Puskas, MD, dated Oct. 11, 2005, 7 pgs.

Ramsay et al., "Vagus Nerve Stimulation for Treatment of Partial Seizures: 2. Safety, Side Effects, and Tolerability," Epilepsia, 1994; 35(3):627-636.

Randall et al., "Functional Anatomy of the Cardiac Efferent Innervation," Neurocardiology, 1988; pp. 3-24.

Reid, "Surgical Technique for Implantation of the Neurocybernetic Prosthesis," Epilepsia, 1990; 31(Suppl. 2):S38-S39.

Rosenqvist et al., "Relative Importance of Activation Sequence Compared to Atrioventricular Synchrony in Left Ventricular Function," The American Journal of Cardiology, Jan. 15, 1991; 67:148-156.

Rossi et al., "Endocardial Vagal Atrioventricular Node Stimulation in Humans: Reproducibility on 18-Month Follow-up," Europace, 2010; 12:1719-1724. Published online on Sep. 27, 2010.

Roy et al., "Rhythm Control Versus Rate Control for Atrial Fibrillation and Heart Failure," The New England Journal of Medicine, Jun. 19, 2008; 358(25):2667-2677.

Rutecki, "Anatomical, Physiological, and Theoretical Basis for the Antiepileptic Effect of Vagus Nerve Stimulation," Epilepsia, 1990; 31(Suppl. 2):S1-S6.

(56) References Cited

OTHER PUBLICATIONS

Saksena et al., "Prevention of Atrial Fibrillation by Pacing," Chapter 6 in *Recent Advances in Cardiac Pacing: Goals for the 21st Century*, Barold et al., Eds., 1998, Armonk, NY. Cover page, copyright page and pp. 101-114.
Sato et al., "Age-Related Changes of Cardiac Control Function in Man," *Journal of Gerontology*, 1981; 36(5):564-572.
Schwartz et al., "Long Term Vagal Stimulation in Patients with Advanced Heart Failure: First Experience in Man," *European Journal of Heart Failure*, 2008; 10:884-891.
Severtson et a., "Vagal Nerve Monitoring: A Comparison of Techniques in a Canine Model," *American Journal of Otology*, 1997; 18(3):398-400.
Sharma et al., "The Importance of Tumor Necrosis Factor and Lipoproteins in the Pathogenesis of Chronic Heart Failure," *Heart Failure Monitor*, 2001; 2(2):42-47.
Shishehbor et al., "Inflammation: Implications for Understanding the Heart-Brain Connection," *Cleveland Clinic Journal of Medicine*, Feb. 2007; 74(Suppl 1): S37-S41.
Subramanian, "Clinical Experience with Minimally Invasive Reoperative Coronary Bypass Surgery," *Eur. J. Cardio-Thorac. Surg.*, 1996, 10:1058-1062. (Abstract Only).
Tan et al., "Cardiac Myocyte Necrosis Induced by Angiotensin II," *Circulation Research*, 1991; 69(5):1185-1195.
Tarver et al., "Clinical Experience with a Helical Bipolar Stimulating Lead," *PACE*, Oct. 1992; 15(10 PartII):1545-1556.
Taylor, "Anticholinesterase Agents," Goodman and Gilman's Pharmacological Basis of Therapeutics, 6th Ed. MacMillian Publishing Co., Inc., New York, 1980; pp. 93, 94, and 104-108.
Taylor, "Multiple-electrode Nerve Cuffs for Low-velocity and Velocity-selective Neural Recording," *Med. Biol. Eng. Comput.*, 2004; 42:634-643.
Terry et al., "An Implantable Neurocybernetic Prosthesis System," *Epilepsia*, 1990; 31(Suppl. 2):S33-S37.
Thompson et al., "Bradycardia Induced by Intravascular Versus Direct Stimulation of the Vagus Nerve," *Ann. Thorac. Surg.*, 1998; 65:637-642.
Tosato et al., "Closed-loop Control of the Heart Rate by Electrical Stimulation of the Vagus Nerve," *Med. Biol. Eng. Comput.*, 2006; 44:161-169.
Tougas et al., "Effects of Chronic Left Vagal Stimulation on Visceral Vagal Function in Man," *PACE*, Oct. 1992; 15(10 PartII):1588-1596.
Tougas et al., "Evidence of Impaired Afferent Vagal Function in Patients with Diabetes Gastroparesis," *PACE*, Oct. 1992; 15(10 PartII):1597-1602.
Tracey, "Physiology and Immunology of the Cholinergic Antiinflaramatory Pathway," *The Journal of Clinical Investigation*, Feb. 2007; 117(2):289-296.
Upton, Editorial, *PACE*, Oct. 1992; 15(10 PartII):1543-1544.
Urthaler, "Experimental Studies on Pathogensis of Asystole After Verapamil in the Dog," *Am. J. Cardiol.*, Oct. 1979; 44(4):651-656 (Abstract Only).
Uthman et al., "Efficacy and Safety of Vagus Nerve Stimulation in Patients with Complex Partial Seizure," *Epilepsia*, 1990, 31(Suppl. 2):S44-S50.
Vardas et al., "AAIR Versus DDDR Pacing in Patients with Impaired Sinus Node Chronotropy: An Echocardiographic and Cardiopulmonary Study," *PACE*, Jul. 1997; 20:1762-1768.
Watkins et al., "Implications of Immune-to-Brain Communications for Sickness and Pain," *Proc. Natl. Acad. Sci. USA*, Jul. 1999; 96:7710-7713.
Watkins et al., "Glia: A Novel Drug Discovery Target for Clinical Pain," Nature Reviews Drug Discovery, 2003; 2:973-985.
Westaby, "Coronary Surgery Without Cardiopulmonary Bypass," *British Heart Journal*, 1995; 73:203-205.
Wilder, "Vagus Nerve Stimulation for the Control of Epilepsy," Epilepsia, vol. 31, Supplement 2, 1990, pp. S1-S60; Conference Porceedings in conjunction with American Epilepsy Society Annual Meeting, Boston, MA, Dec. 2, 1989. Cover pages, Table of Contents, Foreword, and Summary and Conclusions; 6 pgs. (Each article listed in the Table of Contents is included separately in this Information Disclosure Statement).
Wilkoff et al., "Critical Analysis of Dual-Chamber Implantable Cardioverter-Defibrillator Arrhythmia Detection," *Circulation*, Jan. 23, 2001, 103(3):381-386.
Woodbury et al., "Effects of Vagal Stimulation on Experimentally Induced Seizures in Rats," *Epilepsia*, 1990; 31(Suppl. 2):S7-S19.
Yeh et al., "Geriatric Cachexia: The Role of Cytokines," *Am. J Clin. Nutr.*, 1999; 70:183-197.
Yokoyama et al., "Tumor Necrosis Factor-α Provokes a Hypertrophic Growth Response in Adult Cardiac Myocytes," *Circulatio*, 1997; 95:1247-1252.
Yokoyama et al., "Cellular Basis for the Negative Inotropic Effects of Tumor Necrosis Factor-α in the Adult Mammalian Heart," *The Journal of Clinical Investigation*, Nov. 1993; 92:2303-2312.
Zhang et al., "Chronic Atrioventricular Nodal Vagal Stimulation: First Evidence for Long-Term Ventricular Rate Control in Canine Atrial Fibrillation Model," *Circulation*, 2005; 112:2904-2911.
Zhuang et al., "Ventricular Rate Control by Selective Vagal Stimulation is Superior to Rhythm Regularization by Atrioventricular Nodal Ablation and Pacing During Atrial Fibrillation," *Circulation*, 2002; 106:1853-1858.
American Heart Association definition of Atrial or Supraventricular Tachycardia, http://www.heart.org/HEARTORG/Conditions/Arrhythmia/AboutArrhythmia/Thachycardia_UCM_302018_Article.jsp. Content last reviewed May 13, 2012. Copyright 2013. 2 pages.

\* cited by examiner

THERAPY USING PERTURBATION AND EFFECT OF PHYSIOLOGICAL SYSTEMS

The disclosure herein relates to methods for treating a patient, and further to devices for performing such treatment.

Sensory information is sent from the periphery (e.g., organs, etc.) of a patient to the patient's brain (i.e., afferent electrical activity) and from the patient's brain to the periphery (i.e., efferent electrical activity) over one or more nerve fibers. Such sensory information may be indicative of the functionality of various physiological systems of a patient.

The use of nerve stimulation, e.g., stimulation of the vagus nerve, for treating and controlling a variety of medical, psychiatric, and neurological disorders has seen significant growth over the last several decades, e.g., including the treatment of heart conditions. For example, United States Patent Publication 20070299476, published Dec. 27, 2007, by Park et al., discloses delivering electrical stimulation to a sympathetic afferent nerve, acquiring information indicative of autonomic tone and, based at least in part on the information, and determining if the delivering caused an increase in parasympathetic nerve activity. Generally, nerves are composed of somatic and visceral afferent fibers (which, e.g., convey impulses toward the brain) and efferent fibers (which, e.g., convey impulses to an effector in the periphery to regulate activity such as, for example, heart activity, muscle contraction, or glandular secretion).

SUMMARY

The disclosure herein relates generally to methods and devices for use in treating a patient by utilizing a response index associated with a selected organ. The selected organ may be assessed by comparing the response index to physiological parameters monitored in response to one or more perturbations. For example, the status of the selected organ may be assessed by comparing the relationship between one or more perturbations (e.g., electrical stimulation of the efferent vagus nerve) and one or more effects associated with the one or more perturbations (e.g., electrical activity effect of the vagus nerve, effect on the sympathetic efferent pathways, etc.). Information derived by the comparisons using the response index may be used to initiate or adjust therapy delivered by medical devices such as an implantable medical device (IMD) (e.g., a pacemaker (PM), an implantable cardioverter defibrillator (ICD), neuromodulation system, neurostimulator, etc.).

One exemplary device for use in treatment of a patient disclosed herein includes: monitoring apparatus, a sensing module, a therapy delivery module, and a control module. The monitoring apparatus is configured to monitor physiological parameters of a patient and includes at least one electrode to monitor the electrical activity of at least one nerve associated with a selected organ of the patient (e.g., the heart, the kidney, the stomach, the gastrointestinal tract (or one or more portions thereof), one or more muscles, etc.). The sensing module is coupled to the monitoring apparatus and configured to receive the monitored physiological parameters. The therapy delivery module is configured to deliver therapy to the patient. The control module is coupled to the sensing module and to the therapy delivery module. Further, the control module is configured to monitor physiological parameters of the patient using the monitoring apparatus and provide a response index comprising data representative of electrical activity effect (e.g., the afferent electrical activity) of the at least one nerve associated with the selected organ as caused by one or more perturbations to one or more physiological systems. The control module is further configured to assess a status of the selected organ by comparing the response index with the physiological parameters monitored after at least one physiological system of the patient has been perturbed and deliver therapy to the patient based on the assessed status of the selected organ.

In one or more embodiments of the devices disclosed herein, the exemplary devices further include perturbation apparatus coupled to the control module and configured to perturb at least one physiological system of the patient, and the control module is further configured to perturb at least one physiological system of the patient using the perturbation apparatus. Further, the perturbation apparatus may include at least one electrode to stimulate at least one anatomical structure associated with the selected organ of the patient.

Further, in one or more embodiments of the devices disclosed herein, the data representative of electrical activity effect of the at least one nerve associated with the selected organ includes data representative of an indirect component of a compound action potential (CAP) between a perturbation of the at least one physiological system and electrical activity of the at least one nerve associated with the selected organ. A CAP is a momentary change in electrical potential on the surface of a cell, especially of a nerve cell, that occurs when it is stimulated, resulting in the transmission of an electrical impulse. An indirect component of a CAP is described or depicted by an expected latency and/or dispersion. Further, the data representative of electrical activity effect of the at least one nerve associated with the selected organ may include data representative of expected baseline effects on the selected organ caused by the perturbation to at least one physiological system. Still further, the data representative of electrical activity effect of the at least one nerve associated with the selected organ may include data representative of an expected relationship between a perturbation of the at least one physiological system and electrical activity of the at least one nerve associated with the selected organ. Yet still further, the response index may include data based on activity levels of the patient.

Another exemplary device for use in treatment of a patient disclosed herein includes: perturbation apparatus, monitoring apparatus, a sensing module, a therapy delivery module, and a control module. The perturbation apparatus is configured to perturb at least one physiological system of a patient and includes at least one electrode to stimulate the patient's vagus nerve. The monitoring apparatus is configured to monitor physiological parameters of the patient and includes at least one electrode to monitor the electrical activity of the patient's vagus nerve. The sensing module is coupled to the monitoring apparatus and configured to receive the monitored physiological parameters. The therapy delivery module is configured to deliver therapy to the patient. The control module is coupled to the perturbation apparatus, to the sensing module, and to the therapy delivery module. Further, the control module is configured to perturb at least one physiological system of the patient using the perturbation apparatus by at least delivering electrical stimulation to the patient's vagus nerve and to monitor physiological parameters of the patient by at least monitoring electrical activity of the patient's vagus nerve. The control module is further configured to provide a response index comprising data representative of electrical activity effect of the vagus nerve (e.g., afferent electrical activity) as caused by one or more perturbations to the vagus nerve, assess a status of the patient's heart by comparing the response index with the physiological parameters monitored after perturbing at least one physiological system of the patient, and deliver therapy to the patient using the therapy delivery module based on the assessed status of the patient's heart (e.g., initiating the delivery of therapy to the patient's heart, adjusting the therapy being delivered to the patient's heart, delivering at least one of vagal stimulation and heart pacing therapy, etc.).

In one or more embodiments of the devices disclosed herein, the data representative of electrical activity effect of the vagus nerve includes data representative of an indirect component of a CAP between a perturbation of the at least one physiological system and electrical activity of the vagus nerve associated with the heart. Further, the data representative of electrical activity effect of the vagus nerve may include data representative of an expected baseline effect on the heart caused by the perturbation to the at least one physiological system. Still further, the data representative of electrical activity effect of the vagus nerve may include data representative of an expected relationship between a perturbation of the at least one physiological system and electrical activity of the vagus nerve associated with the heart.

One exemplary method for use in treatment of a patient disclosed herein includes perturbing at least one physiological system of the patient and monitoring physiological parameters of the patient. Monitoring physiological parameters of the patient includes monitoring electrical activity of at least one nerve associated with a selected organ of the patient (e.g., the heart, the kidney, the stomach, the gastrointestinal tract, one or more muscles, etc.). The exemplary method further includes providing a response index that includes data representative of electrical activity effect (e.g., afferent electrical activity effect) of the at least one nerve associated with the selected organ as caused by one or more perturbations to one or more physiological systems, assessing a status of the selected organ by comparing the response index with the physiological parameters monitored after perturbing at least one physiological system of the patient, and delivering therapy to the patient based on the assessed status of the selected organ.

In one or more embodiments of the methods disclosed herein, the data representative of electrical activity effect of the at least one nerve associated with the selected organ includes data representative of an expected latency between a perturbation of the at least one physiological system and electrical activity of the at least one nerve associated with the selected organ. Further, the data representative of electrical activity effect of the at least one nerve associated with the selected organ may include data representative of expected baseline effects on the selected organ caused by the perturbation to at least one physiological system. Still further, the data representative of electrical activity effect of the at least one nerve associated with the selected organ may include data representative of an expected relationship between a perturbation of the at least one physiological system and electrical activity of the at least one nerve associated with the selected organ.

Another exemplary method for use in treatment of a patient disclosed herein includes perturbing at least one physiological system of the patient. Perturbing at least one physiological system of the patient includes delivering electrical stimulation to the patient's vagus nerve. The exemplary method further includes monitoring physiological parameters of the patient (e.g., monitoring electrical activity of the patient's vagus nerve, monitoring the afferent electrical activity of the patient's vagus nerve, etc.) and providing a response index that includes data representative of electrical activity effect of the vagus nerve (e.g., afferent electrical activity effect of the vagus nerve) as caused by one or more perturbations to the vagus nerve. The exemplary method further includes assessing a status of the patient's heart by comparing the response index with the physiological parameters monitored after perturbing at least one physiological system of the patient and delivering therapy to the patient based on the assessed status of the patient's heart (e.g., initiating the delivery of therapy to the patient's heart, adjusting the therapy being delivered to the patient's heart, delivering at least one of vagal stimulation and heart pacing therapy, etc.).

In one or more embodiments of the methods disclosed herein, the data representative of electrical activity effect of the vagus nerve includes data representative of an expected latency between a perturbation of the at least one physiological system and electrical activity of the vagus nerve associated with the heart. Further, the data representative of electrical activity effect of the vagus nerve may include data representative of an expected baseline effect on the heart caused by the perturbation to the at least one physiological system. Still further, the data representative of electrical activity effect of the vagus nerve may include data representative of an expected relationship between a perturbation of the at least one physiological system and electrical activity of the vagus nerve associated with the heart.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1:
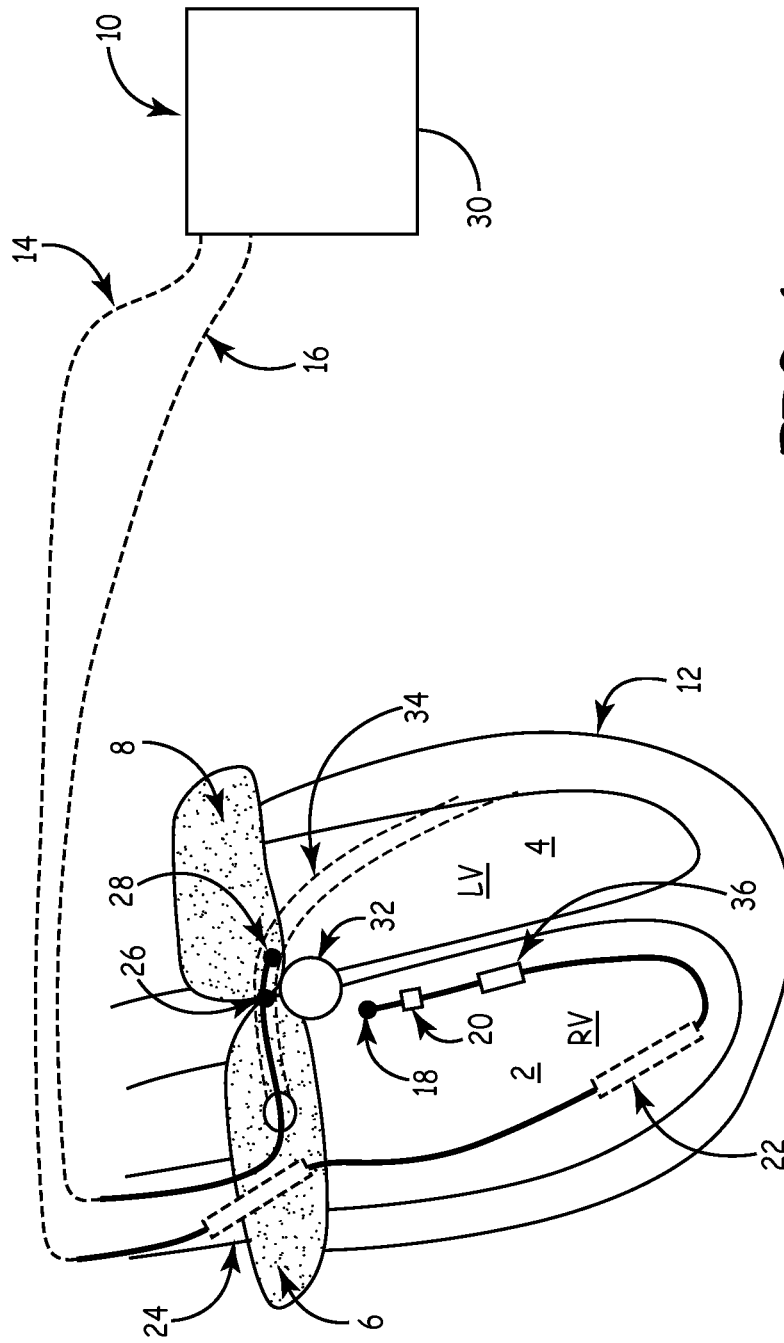
FIG. 1 is a schematic diagram of an implantable medical device (IMD) operably coupled to a patient's heart.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary methods, devices, and systems shall be described herein with reference to FIGS. 1-11. Elements or processes from one embodiment may be used in combination with elements or processes of the other embodiments; and, the possible embodiments of such methods, devices, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

The methods described herein may be implemented by one or more various devices (e.g., implantable medical devices) and systems. Such devices and systems may include one or more leads, electronic circuits, power sources, sensors, electrodes, fluid delivery devices, etc. One example of a medical device that may be used in carrying out the methods described herein is depicted in FIG. 1 as a schematic diagram of an implantable medical device 10 (IMD). Although IMD 10 is depicted with reference to a patient's heart 12, the devices and methods described herein may be used with any physiological system or organ of a patient. Alternative exemplary devices capable of implementing monitoring and/or delivery of perturbation (e.g. electrical stimuli etc.) and/or therapy can include the Implantable Neurostimulator Device described in U.S. Pat. No. 7,555,345 to Carl Wahlstrand et al. or the combined neurostimulator and cardiac stimulator described in US Patent Application 2010-0114208 (application Ser. No. 12/362,792 filed Jan. 30, 2009), the disclosures of which are incorporated by reference in their entireties.

The IMD 10 may be configured to monitor one or more physiological parameters of a patient. In this embodiments, since the IMD 10 is configured to monitor physiological parameters with respect to a patient's heart, electrical activity of a patient's nerve (e.g. vagus nerve etc.), the electrical activity of a patient's heart, chemical activity of the patient's heart, hemodynamic activity of a patient's heart, etc. The monitored physiological parameters, in turn, may be used by the IMD 10 for the various methods described herein, e.g., to measure or determine a status of an organ. In one or more embodiments, IMD 10 is configured to measure or determine an effect caused by a perturbation to one or more physiological systems (e.g. organ (e.g. heart, stomach etc.), organ-nerve system etc.

Further, in one or more embodiments, the IMD may be capable of delivering therapy to various organs and/or physiological systems of the patient. Since this IMD 10 is configured with respect to the patient's heart, such therapy may include delivering vagal stimulation (e.g., electrical stimulation to a patient's vagus nerve), electrical stimulation for pacing the patient's heart 12 (e.g., bradycardia pacing, cardiac resynchronization therapy, anti-tachycardia pacing (ATP)), high-energy shock pulses for cardioversion/defibrillation therapy, etc.

As used herein, "stimulation of the vagus nerve," also referred to herein simply as "vagal stimulation," refers to stimulation of neural tissue innervating the myocardium, directly or indirectly, e.g., stimulation of one or more of the vagus nerves or its branches (e.g., including the afferent and/or efferent fibers), the sinoatrial (SA) nodal fatty pad, the atrioventricular (AV) nodal fatty pad and along the great vein, the cervical vagus nerve (e.g., the right or left side), the fat pad located between the medial superior vena cava and aortic root (SVC-Ao fat pad), the fat pad superior to the right pulmonary artery, the fat pad at the IVC-left atrial junction (IVC-LA fat pad), the fat pad proximate the right pulmonary vein-atrial junction (RPV fat pad), the spinal cord (e.g., vertebral levels T1-T12, C1-C8, etc. such as described in U.S. Pat. App. Pub. No. 2002/0107552 A1 to Hill et al., which is incorporated herein by reference in its entirety), and additional intracardiac locations near the SA node, AV node, coronary sinus, and base of the right ventricle.

The IMD 10, as shown, is configured to monitor physiological parameters of the patient and to deliver therapy using two leads. Although the IMD 10 depicted in FIG. 1 only uses two leads, a single lead or more than two leads may be used with the methods and devices described herein. For example, the IMD 10 may use one lead that includes a single electrode positionable near the atrioventricular node in the base of the right ventricle. The single electrode may be used for both atrial/ventricular pacing/sensing and vagal recording/stimulation.

As shown, the IMD 10 is coupled to two transvenous leads: a right ventricular (RV) lead 14 and a coronary sinus (CS) lead 16. RV lead 14 includes a distal tip electrode 18 deployed in the basal region of the right ventricle 2 in operative relation to the AV node 32. Ring electrode 20 is spaced proximally from tip electrode 18 for use in bipolar sensing and pacing in the right ventricle 2. According to one embodiment, tip electrode 18 may be used in conjunction with IMD housing 30 (for unipolar sense/stimulation) or ring electrode 20 (for bipolar sense/stimulation) for sensing ventricular signals, for detecting a ventricular rhythm, for delivering cardiac pacing pulses in the right ventricle, for monitoring the ST segment, for recording/monitoring the electrical activity of the vagus nerve, and for delivering vagal stimulation pulses in the right ventricle. RV lead 14 may further include coil electrodes 22 and 24 for use in delivering high-energy shock pulses for cardioversion and defibrillation therapies. Other embodiments may include additional electrodes adapted for sensing and stimulating the right atrium 6, either on a separate right atrial lead or included along RV lead 14, recording the electrical activity of various nerves (e.g., the vagus nerve), etc. Further, such electrodes may be positioned relative to the SA node and/or AV node for vagal stimulation or for recording/monitoring of the electrical activity of the vagus nerve (e.g., portions of the vagus nerve located proximate the heart 12).

RV lead 14 may further includes sensor 36 used for sensing signals other than cardiac electrical signals, such as mechanical signals, e.g., accelerometer sensing, hemodynamic activity, flow, myocardial acceleration, heart sound, tissue perfusion, lung fluid status, etc., or blood chemistry signals, e.g., temperature, oxygen saturation, pH, etc. In one embodiment, sensor 36 is embodied as a pressure sensor (e.g., for monitoring various blood pressures and pressure drops) to, e.g., be used in verifying effective vagal stimulation. Further, for example, sensor 36 may be an oxygen sensor, as disclosed in U.S. Pat. No. 4,750,495 issued to Moore et al. on Jul. 31, 1989, a pressure transducer as disclosed in U.S. Pat. No. 4,485,813 issued to Anderson et al. on Dec. 4, 1984, a physical activity sensor as disclosed in U.S. Pat. No. 4,428,378, issued to Anderson et al on Jan. 31, 1984, or a ventricular impedance plethysmograph as disclosed in U.S. Pat. No. 4,535,774 issued to Olson on Aug. 20, 1985, all of which are incorporated herein by reference in their entireties.

Coronary sinus lead 16 may be deployed in a cardiac vein 34 via the coronary sinus for positioning electrodes 26 and 28 in operative relation to the left chambers of heart 12. In particular, in one embodiment, electrodes 26 and 28 are positioned near the AV node 32 to, e.g., for blocking conduction of the AV node 32, etc. Further, electrode 26 may be positioned proximate the coronary sinus. Electrodes 26 and 28 may also be used for sensing cardiac signals and for delivering cardiac pacing pulses in the left ventricle 4. It is recognized that coronary sinus lead 16 may carry additional electrodes such as a coil electrode for use in delivering high energy shock pulses, additional ring electrodes, and/or a tip electrode for cardiac sensing and pacing in the left atrium 8.

Furthermore, the embodiments described herein are not limited for use with transvenous leads as shown in FIG. 1. For example, other embodiments may include the use of epicardial electrodes positioned in operative relation to the fatty pad near the SA node and/or the fatty pad near the AV node. Further, subcutaneous electrodes may be incorporated on the housing 30 of IMD 10 and/or positioned on subcutaneous leads extending from IMD 10 for use in sensing cardiac signals and delivering electrical stimulation pulses, e.g., for delivering cardiac pacing and shock therapies. Numerous alternative electrode configurations may be appropriate for vagal stimulation, including endocardial or epicardial electrodes deployed near or adjacent the SA nodal and/or AV nodal fatty pads or electrodes positioned along the vagus nerve branches.

Figure 2:
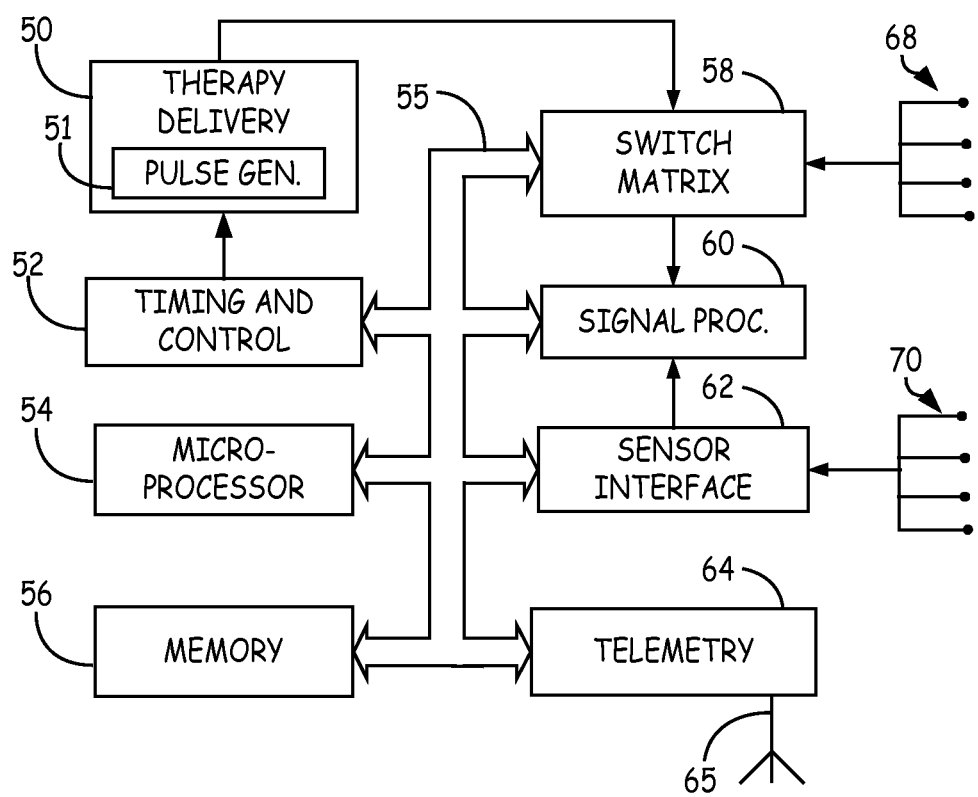
FIG. 2 is a block diagram of the IMD shown in FIG. 1.

FIG. 2 is a functional block diagram of IMD 10 shown in FIG. 1. IMD 10 generally includes timing and control circuitry 52 and an operating system that may employ microprocessor 54 or a digital state machine for timing sensing and therapy delivery functions and controlling other device functions in accordance with a programmed operating mode. Microprocessor 54 and associated memory 56 are coupled to the various components of IMD 10 via a data/address bus 55. IMD 10 includes therapy delivery module 50 for delivering a therapy, such as an electrical stimulation or drug therapy, under the control of timing and control circuitry 52. Therapy delivery module 50 includes pulse-generating circuitry 51 for generating electrical stimulation pulses (e.g., bursts of electrical stimulation pulses) under the control of timing and control circuitry 52. As described herein, pulse-generating circuitry 51 generates electrical stimulation pulses, e.g., for stimulating the vagus nerve.

Further, the therapy delivery module 50 may also be used to deliver perturbation to one or more physiological systems of the patient. For example, the therapy delivery module 50 may deliver electrical stimulation to the patient's vagus nerve for in the methods described herein as well as for delivering therapy. For convenience, the portion of the IMD 10 that delivers perturbation may be referred to as a "perturbation module," but may be part of the therapy delivery module configured. In other embodiments, however, the perturbation module may not be part of the therapy delivery module.

For delivering electrical stimulation pulses, pulse-generating circuitry 51 may be coupled to two or more electrodes 68 via a switch matrix 58. Switch matrix 58 is used for selecting which electrodes and corresponding polarities are used for delivering electrical stimulation pulses. Electrodes 68 may include lead-based electrodes, leadless electrodes incorporated on IMD 10, and/or the IMD housing configured for use as a can or case electrode. Therapy delivery module 50 may further include high voltage circuitry for generating high voltage cardioversion/defibrillation shocks. Aspects of the present disclosure may be embodied in an implantable cardioverter defibrillator including high voltage circuitry as generally disclosed in U.S. Pat. No. 6,731,978 to Olson et al., incorporated herein by reference in its entirety.

Electrodes 68 may also be used for sensing electrical signals within the body, such as cardiac signals and/or nerve signals. Cardiac electrical signals are sensed using any of electrodes 68 for detecting the heart rhythm and determining when and what therapy is needed, and in controlling the timing of stimulation pulses. In other words, the IMD 10 includes monitoring apparatus, which includes electrodes 68 amongst other things. As will be described herein, cardiac electrical signals may be sensed following delivery of vagal stimulation for adjusting the vagal stimulation, for verifying the effectiveness of the vagal stimulation, and/or for detecting, and/or discriminating between cardiac conditions (e.g., SVT, VT/VF, etc.). Nerve signals are sensed using any of the electrodes 68 for detecting the electrical activity (e.g., parasympathetic activity, etc.) of various nerves.

Electrodes used for sensing and electrodes used for stimulation may be selected via switch matrix 58. When used for sensing, electrodes 68 are coupled to signal processing circuitry 60 via switch matrix 58. Processing circuitry 60 includes sense amplifiers and may include other signal conditioning circuitry and an analog to digital converter. In other words, the IMD 10 may include a sensing module, e.g., that includes switch matrix 58, signal processing circuitry 60, etc. Electrically sensed signals may then be used by microprocessor 54 for detecting physiological events, such as detecting and discriminating cardiac arrhythmias.

The monitoring apparatus of the IMD 10 may further include sensors 70 such as pressure sensors, accelerometers, flow sensors, blood chemistry sensors, activity sensors, and/or other physiological sensors known for use with IMDs. Sensors 70 are coupled to IMD 10 via a sensor interface 62 which provides sensor signals to signal processing circuitry 60. Sensor signals are used by microprocessor 54 for detecting physiological events or conditions. For example, IMD 10 may monitor heart wall motion, blood pressure, blood chemistry, respiration, and/or patient activity. Monitored signals may be used for sensing the need for delivering, adjusting, terminating, and/or initiating therapy under control of the operating system and microprocessor 54.

The operating system includes associated memory 56 for storing a variety of programmed-in operating mode and parameter values that are used by microprocessor 54. The memory 56 may also be used for storing data, e.g., data for a response index, data compiled from sensed signals and/or relating to device operating history (e.g., for use in delivering, adjusting, controlling, initiating, and/or terminating therapy), and/or data for communicating such data outside of the patient (e.g., using telemetry communication out of recorded history on receipt of a retrieval or interrogation instruction). In other words, the IMD 10 may include a control module, which may include the microprocessor 54 and memory 56 and may be configured using an operating system.

IMD 10 further includes telemetry circuitry 64 and antenna 65. Programming commands or data are transmitted during uplink or downlink telemetry between IMD telemetry circuitry 64 and external telemetry circuitry included in a programmer or home monitoring unit.

Figure 3:
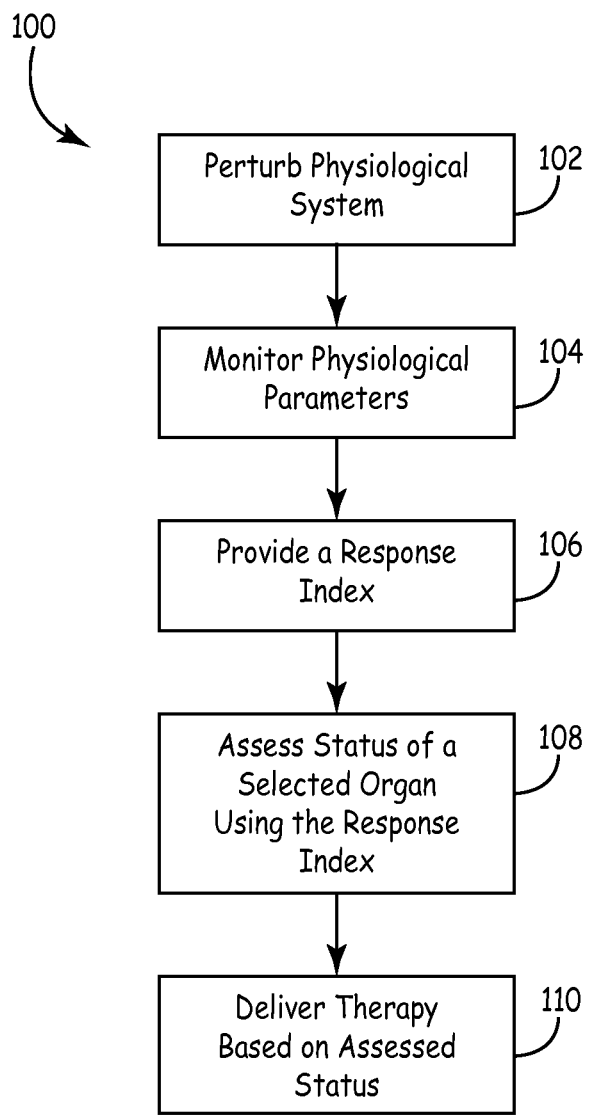
FIG. 3 is a flow chart depicting an exemplary method for use in treating a patient by, e.g., perturbing a physiological system and assessing the effect of the perturbation.

A generalized method 100 for use in treating a patient is diagrammatically depicted in FIG. 3. Generally, method 100 may include perturbing at least one physiological system of a patient 102, measuring an effect 104, 106, 108 (e.g., caused by the perturbation), and delivering therapy to a portion of the patient based on the measured effect 110.

The method 100 may be used to treat a selected organ of a patient. In at least one embodiment, the method 100 may be used to treat a patient's heart, e.g., as described in more detail herein with reference to the method 300 of FIG. 5. Processes

102, 104, 106, 108, 110 will be described in further detail herein with respect to one or more selected organs.

Further, method 100 is intended to illustrate the general functional operation of the devices described herein, and should not be construed as reflective of a specific form of software or hardware necessary to practice all of the methods described herein. It is believed that the particular form of software will be determined primarily by the particular device architecture employed in the device and by the particular detection and therapy delivery methodologies employed by the device and/or system. Providing software and/or hardware to accomplish the described methods in the context of any modern medical device (e.g., an IMD), given the disclosure herein, is within the abilities of one of skill in the art.

Further, methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

The hardware used to accomplish the described methods, may include any one or more of a microprocessor, a digital signal processor (DSP), a controller, an application specific integrated circuit (ASIC), a field programmable gate array (FPGA), or equivalent discrete or integrated logic circuitry. In one or more exemplary embodiments, the processor may include multiple components, such as any combination of one or more microprocessors, one or more controllers, one or more DSPs, one or more ASICs, or one or more FPGAs, as well as other discrete or integrated logic circuitry. The functions and processes described herein may be embodied as software, firmware, hardware, or any combination thereof.

The method 100 of FIG. 3 includes perturbing at least one physiological system of a patient 102. The physiological system may be any one or more systems of the human body and/or one or more portions of the physiological system (e.g., one or more organs or portions of organs) that may be capable of being affected by one or more perturbations that may cause one or more detectable effects. For example, the physiological system to be perturbed may be the cardiovascular system (or more specifically, the heart and/or portions of the nervous system innervating the heart), a muscular system (or more specifically, a specific muscle and/or muscle group and/or portions of the nervous system innervating such muscles and/or muscle groups), the digestive system (or, more specifically the stomach and/or portions of the nervous system innervating the stomach), etc.

The perturbation of the at least one physiological system 102 may include delivery of stimulation to the efferent or afferent pathways of one or more nerves (e.g., the vagus nerve), delivery of stimulation to the baroreceptors of one or more bloods vessels, delivery of pacing therapy to a patient's heart (e.g., perturbing the A-V interval, the V-V interval, heart rate variability, heart rate turbulence, T-wave alternans, etc.), inducing a pressure in one or more portions of the patient (e.g., through the injection of drugs or through a change in body position), and/or the initiation of various physiological changes (e.g., through a change in activity, change in body position, change in heart rate, etc.). Further, when stimulation is delivered as a perturbation, the stimulation may include the delivery of electrical stimulation, delivery of drugs, etc. Still further, the perturbation may be delivered during (e.g., synchronized to) selected portions of the cardiac cycle.

Further, electrical stimulation as a perturbation, e.g., to one or more nerves, may be delivered in many different ways. For example, the electrical stimulation may be delivered in bursts of pulses of electrical stimulation at various parameters. Such parameters may include time (e.g., the stimulation may be delivered for a selected time constant, e.g., 30 seconds), voltage (e.g., within a range of about 1 volt and about 8 volts), frequency of the pulses within a burst of pulses (e.g., within a range of about 1 hertz to about 150 hertz), frequency of the bursts (e.g., within a range of about 1 hertz to about 100 hertz), pulse width of each pulse (e.g., within a range of about 0.05 milliseconds (ms) to about 1.5 ms), and number of pulses per burst (e.g., within a range of about 3 pulses to about 20 pulses), etc.

In at least one embodiment, where the perturbation includes delivering electrical stimulation to a patient's vagus nerve (which may be referred to herein as "vagal stimulation"), the vagal stimulation may be delivered to neural tissue innervating the myocardium, directly or indirectly, e.g., including the vagus nerve or its branches, the SA nodal fatty pad, the AV nodal fatty pad and along the great vein, the cervical vagus nerve (e.g., right or left side), the fat pad located between the medial superior vena cava and aortic root (SVC-Ao fat pad), and additional intracardiac locations near the SA node, AV node, coronary sinus, and base of the right ventricle.

The method 100 further includes monitoring physiological parameters of the patient 104. For example, monitoring physiological parameters of the patient 104 may include monitoring the electrical activity of at least one nerve associated with a selected organ of the patient. The selected organ is the organ to be analyzed and/or treated by method 100. The selected organ may be, e.g., the heart, the kidney, the stomach, the gastrointestinal tract, one or more muscles or muscle groups, etc. In the example where the selected organ is the heart, the at least one nerve associated with the heart (i.e., the selected organ) may be the vagus nerve. The physiological parameters may be monitored 104 before, during, and/or after the perturbation of the physiological system 102.

Further, monitoring physiological parameters of the patient may include additional monitoring other than monitoring the electrical activity of at least one nerve associated with the selected organ of the patient. For example, monitoring physiological parameters of a patient may include monitoring the electrical activity of the selected organ, the chemical activity of the selected organ, the pressure activity of the selected organ, the physical movement (e.g., using an accelerometer) of portions of the selected organ, etc.

The electrical activity of a selected organ may include one or more signals that may be monitored (e.g., using electrodes) from locations in or around the selected organ. Using such monitored electrical activity of the selected organ, certain metrics may be determined and collected (e.g., for analysis). For example, when the selected organ is the heart, the following metrics may be determined and collected using the electrical activity of the patient's heart: heart rate (HR), heart rate variability (HRV), heart rate turbulence (HRT), deceleration/acceleration capacity, deceleration sequence incidence, T-wave alternans (TWA), electrocardiogram, P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment, T-wave changes, QT intervals, electrical vectors, etc. Further, for example, multiple graphs displaying cardiovascular effect data as caused by perturbation are shown in FIG. 8.

The chemical activity of the selected organ may include one or more chemical properties that may be monitored (e.g., using various sensors) from locations in or around the selected organ. Using such monitored chemical activity of the selected organ, certain metrics may be determined and collected (e.g., for analysis). For example, when the selected organ is the heart, the following metrics may be determined and collected using the chemical activity of the patient's heart: oxygen saturation, brain natriuretic peptide (BNP) (proteins/peptides) content, pH, lung fluid status, blood electrolytes (K+, Ca++, Na+, etc.), etc.

The pressure activity of a selected organ may include one or more pressures that may be monitored (e.g., using various sensors) from locations in or around the selected organ and/or in or around (e.g., outside of) the patient's body. Using such monitored pressures of the selected organ, certain metrics may be determined and collected (e.g., for analysis). For example, when the selected organ is the heart, the following pressure activity metrics may be determined and collected (e.g., using Medtronic OptiVol Fluid Status Monitoring): mean arterial pressure, diastolic blood pressure, systolic blood pressure, flow rates, pressure drops, pulmonary artery pressure, pulmonary capillary wedge pressure, right ventricular systolic pressure, right ventricular diastolic pressure, changes in oxygen saturation of the tissue or blood, changes in the amplitude or timing of heart sounds, changes in intrathoracic impedance (e.g. Medtronic OptiVol Fluid Status Monitoring), changes in intracardiac impedance, heart sounds, lung sounds, tissue perfusion, intracardiac pressure, pulmonary vein pressure, cardiac imaging, shear stress, partial pressure of oxygen, etc.

The method 100 further includes providing a response index 106. The response index includes data representative of the electrical activity effect of the at least one nerve (e.g., the vagus nerve) associated with the selected organ (e.g., the heart) as caused by one or more perturbations to one or more physiological systems. An exemplary perturbation can include burst pacing electrical stimuli to the target site. Burst pacing (e.g. 10-100 Hz; 0.05-1.5 ms, 0-10V) can influence the status of the heart as exemplified by cardiac parameters. Cardiac parameters can include (the rate of change) of R-R interval (RRI), left ventricular pressure ($P_{LV}$), left ventricular contractility (LVC) and P-Q interval (PQI) or blood values $P_{O2}$ for the heart. For other organs, organ specific blood values can be used.

Another exemplary perturbation can include a low frequency burst of electrical stimuli to the target site. A low frequency burst can be, for example, one pulse per cycle of electrical stimuli at a frequency of about 0.5 Hertz (HZ) to about 10 Hz. During chronic stimulation, cardiac parameters can change for less than a minute but typically, one or more of these cardiac parameters return to baseline value levels due to reflex/sympathetic mechanisms.

Each single pulse can evoke a CAP from fibers of the vagal nerve. A CAP is a momentary change in electrical potential on the surface of a cell, such as a surface of a nerve or muscle cell, that occurs when the surface is stimulated, resulting in the transmission of an electrical impulse. Each CAP can contain one or more direct and indirect components. A single CAP or an average of two or more CAPs can cause one or more peaks in amplitude over time. Typically, a threshold stimulus is surpassed to create a CAP. The CAP continues to increase as the intensity of the stimulus increases (i.e. suprathreshold) until a maximal stimulus causes a maximum response. Any stimulus stronger than the maximal stimulus is called a supramaximal and does not result in any larger a CAP than the maximum response caused by the maximal stimulus.

Further, the response index may include data representative of particular markers for various diseases or conditions associated with the selected organ. Still further, the response index may include data representative of baseline information for particular operating conditions of the selected organ. In essence, the response index may include any data that may be useful in assessing a selected organ or physiological system that has been perturbed (either directly or indirectly) in process 102.

In other words, the data representative of electrical activity effect of the at least one nerve associated with the selected organ may include data representative of expected baseline effects on the selected organ caused by the perturbation to at least one physiological system. In at least one embodiment, the data representative of electrical activity effect of the at least one nerve associated with the selected organ includes data representative of an expected latency between a perturbation of the at least one physiological system and electrical activity of the at least one nerve associated with the selected organ. Latency is a time period between stimulus and the steepest part of the slope of the fourth indirect component, as shown, for example, in FIG. 6 and described in the accompanying text. Still further, the data representative of electrical activity effect of the at least one nerve associated with the selected organ may include data representative of an expected relationship between a perturbation (e.g., electrical stimulation) of the at least one physiological system and the electrical activity (e.g., the effect) of the at least one nerve associated with the selected organ.

The response index may be predetermined based on data recorded from multiple patients, theoretical data, specific data recorded for a particular patient to be treated, etc. In certain groups of patients with pathology of the cardiac nerves, such as diabetics and patients who have had a myocardial infarct, the baseline response/effects may vary. Further, the baseline response/effects may vary for each particular patient. As such, the response index may be created using an implantable medical device (e.g., after implantation) to test the patient to establish data for the formation of the response index for that particular patient. Further, for example, the response index may be created using data harvested from a plurality of trial studies.

The method 100 further includes assessing a status of the selected organ using the response index 108. Assessing the status of the selected organ 108 may include comparing the response index with the physiological parameters monitored after perturbing at least one physiological system of the patient.

For example, the method 100 may compare a particular monitored physiological parameter to a baseline value (or range of baseline values) indicative of healthy or unhealthy function of the selected organ. If the monitored physiological parameter is not close to the baseline value (or within a range of baseline values), then the method 100 may assess that the selected organ may be either healthy or unhealthy.

Further, for example, the method 100 may compare a particular monitored physiological parameter to a marker value (or range of marker values) indicative of a disease or condition of the selected organ. If the monitored physiological parameter is close to the marker value (or within a range of marker values), then the method 100 may assess that the selected organ may be affected or has been affected by a disease or condition.

After assessment 108, the method 100 may deliver therapy to the patient based on the assessed status of the selected organ 110. Such therapy may be dependent on the selected organ. For example, if the selected organ is the heart, then the method 100 may deliver appropriate therapy (e.g., pacing or vagal stimulation) to treat the particular assessed heart status.

As described herein, the selected organ may be a patient's heart and the electrical activity of the patient's vagus nerve may be monitored to assess the state of the patient's heart after a physiological system of the patient has been perturbed.

Further, in at least one embodiment, the assessment 108 may be used as a tool to select patients who may be candidates (e.g., responders) to a particular type of the therapy. In other words, the assessment 108 may determine if therapy would be effective for a particular patient.

For example, the balance between the sympathetic and the parasympathetic tones may be impacted by the current functional demand of the heart. The inherent time constant differences of the sympathetic nervous system (e.g., longer time constants) and parasympathetic nervous system (e.g., shorter time constants) may provide fine control for changing the cardiac function due to differences in demand. Further, an even longer time constant resides in the neuropeptide system and the ganglionic plexi integration on a selected organ.

During normal heart functionality, a difference in demand due to, e.g., exercise, influences the balance between the sympathetic and parasympathetic nervous systems. The amount that both systems deviate from the average of both systems, however, may not change. In other words, the greater the activity of the parasympathetic system, the smaller the activity of the sympathetic system and the other way around.

Figure 4:
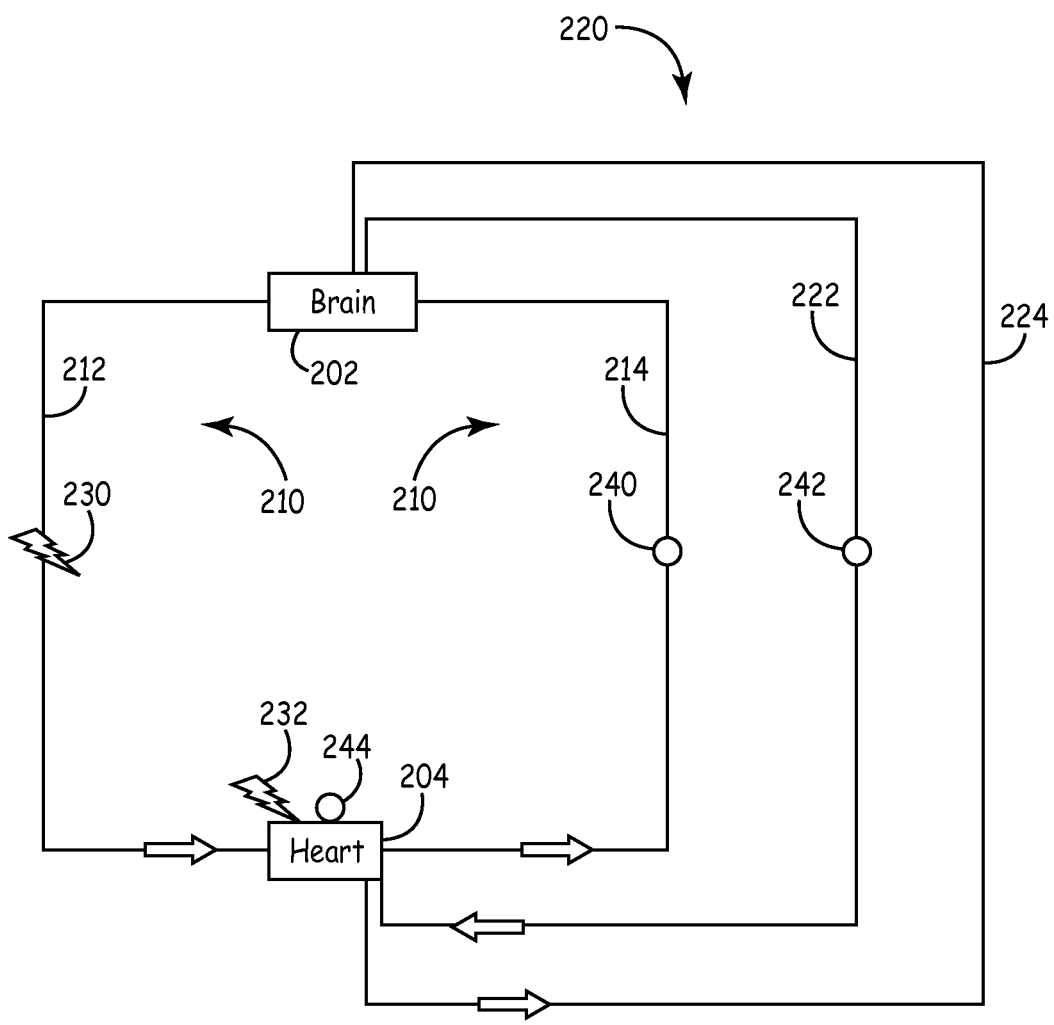
FIG. 4 is a schematic diagram depicting a patient's vagus nerve for use in the description of methods and devices described herein.

A schematic diagram depicting a portion of the patient's nervous system for use in the description of methods and devices set forth herein is depicted in FIG. 4. The brain 202 sends information via the efferent pathway 212 of the vagus nerve 210 to the heart 204 and via the efferent pathway 222 of the ganglionic plexi and spinal cord at vertebral levels C1-C2 220. Conversely, the heart 204 sends information back to the brain 202 via the afferent pathway 214 of the vagus nerve 210 and via the afferent pathway 224 of the ganglionic plexi and spinal cord at vertebral levels C1-C2 220. As such, the cardiovascular system may be considered as a control system consisting of a parasympathetic and sympathetic nervous systems with both afferent and efferent pathways. The functioning of parts of this control system may be influenced by cardiac stress and damage. For example, ischemia, inflammation, and coronary disease may influence signaling in the afferent pathway, and therefore, may also influence the degree of feed-back to the counteracting nervous (parasympathetic or sympathetic) system. Further, for example, diseases such as heart failure, diabetes, and myocardial infarction may influence the intactness of the efferent and afferent pathway in both systems.

The cardiovascular control system could be evaluated by perturbing the system and assessing (e.g., measuring) the effect (e.g., providing a response index). For example, the sympathetic or parasympathetic cardiovascular control system may be evaluated by perturbing the system through stimulation 230 of the efferent pathway 212 of the vagus nerve 210 and relating the stimulus 230 (e.g., electrical stimulation) with a sensed afferent effect 240 along the afferent pathway 214 of the vagus nerve 210. In at least one embodiment, a phase difference may be evaluated between efferent stimulation 230 and afferent effect 240.

Further, for example, the total cardiovascular control system, e.g., the parasympathetic nervous system and its feedback on the sympathetic nervous system, may be evaluated by perturbing the system through stimulation 230 of the efferent pathway 212 of the vagus nerve 210 and relating the stimulus 230 with a sensed efferent effect 242 along the efferent pathway 222 of the ganglionic plexi and spinal cord at vertebral levels C1-C2 220 by relating absolute changes in neural signals between stimulation 230 and effect 242, e.g., by comparing signal properties (e.g. frequency content, signal amplitudes, latency, etc.).

Alterations in the ratio between afferent and efferent signaling may also be a marker of altered cardiac innervation in post-MI, heart transplant, heart failure, or diabetic patients. Further, an alteration in phase difference, for example the amount of firing during a certain phase of the cardiac cycle, may provide information on the relative amount of certain fibers involved and their function.

In at least one embodiment, an implementation of evaluating cardiac function may be to monitor the afferent signaling alone (e.g., in response to a perturbation, without delivery of a perturbation), which may be enhanced in conditions such as ischemia, coronary artery disease, inflammation, or at times of increased susceptibility to arrhythmia. Cardiac ischemia can be determined to be present when, for example, firing of cardiac C-fiber afferent nerves (e.g. conduction velocity is 0.43 m/s etc.) is increased. In one or more other embodiments, cardiac ischemia can be determined to be present when firing of cardiac C-fiber afferent nerves has increased by 10 percent or more from a baseline established for that particular patient. In another embodiment, firing of cardiac C-fiber afferent nerves has increased by 20 percent or more from a baseline established for that particular patient.

In one or more other embodiments, diabetes may be determined to exist in a patient. For example, a patient may be determined to have diabetes if the summary of the afferent electrical activity input to the vagus nerve is less than a baseline (e.g. less than in a patient with increased neuropathy). In diabetic patients, the general level of nerve activity over the cardiac cycle is increased compared to a baseline if nerves are intact compared to patients with less intactness.

A patient can be determined to be in HF based upon the detected electrical response sensed from afferent fiber. In one or more other embodiments, mean sympathetic nerve activity (MSNA) values, expressed as bursts incidence over time (bs/min) and as burst number corrected for HR (bs/100 hb) is increased in heart failure patients. MSNA nerve activity can be measured with a needle approach in a nerve on the lower leg. Heart failure patients exhibited a significant increase in MSNA values (75.8+/−3.0 versus 63.6+/−2.8 bs/100 hb, $P<0.05$) compared to healthy patients). By implementing the method described herein, the function of the efferent and afferent pathway can be separately assessed.

To assess the function of the efferent pathway, the system could be perturbed by stimulating the efferent pathways 212, 222 and assessing the resulting influence on parameters related to the heart 204. For example, the efferent pathways 212, 222 could be stimulated directly, e.g., through electrical stimulation of the vagus nerve, or could be influenced indirectly, e.g., through stimulating the baroreceptors. The effect 244 may be assessed by considering parameters related to the heart 204, such as R-R interval, R-R interval variability (e.g., in the time domain, in the frequency domain, etc.), contraction force, cardiac output, and other hemodynamic parameters or sympathetic outflow. These parameters may be monitored using a PM, an ICD, a Reveal Insertable Cardiac Monitor (ICM), a Chronicle heart monitor, a neural sensor, etc.

To assess the function of the afferent pathway, the cardiovascular system may be stimulated 232 by changing cardiac parameters by, e.g., changing one or more pacing parameters (AV timings, VV timings, rate, etc.) or inducing a physiological change by, e.g., injection of drugs or change in body position. The effect 240 of the stimulus may be determined by assessing the signaling of the afferent pathway 214 of the vagus nerve 212.

Further, in one or more embodiments, the time between (i.e., the latency) stimulus and effect could be assessed to evaluate the function of the fibers conducting the signal. If a change in the control system is detected (e.g., above or below a certain threshold), nerve stimulation, nerve blocking, or other therapies (e.g., cardiac resynchronization therapy (CRT) with varied AV/VV timing) could be initiated, terminated, and/or adjusted to return the control system to baseline levels. If nerve stimulation or blocking is used, such stimulation or blocking may be applied at the same position or at another location of the nerve and/or its branch. Further, nerves may be activated with the opposite action, e.g., to activate the sympathetic nerve if the perturbation of the parasympathetic vagus nerve appears to be increased.

Each of these processes described with respect to FIG. 4, as well as the rest of this disclosure, may be extended to other organs (e.g., the kidney, the baroreceptors, the stomach, etc.) and other physiological systems to, e.g., evaluate disease states or statuses of those particular organs and/or systems (e.g., kidney disease, hypertension, obesity, etc.).

By electrically stimulating (e.g., a perturbation) the vagus nerve or cardiac branch at a low frequency and amplitude (e.g., which may not influence the heart), electrical signals (compound action potentials) along the vagus nerve resulting from the electrical stimulation may be monitored. As described herein with reference to FIG. 6, the latency of particular components (e.g., slow components (still occurring within 20 ms which can be visualized separately if using 50 Hz (0.02 s interpulses distance)) of the electrical signals may be related to particular physiological parameters of the heart such as heart rate, contractility, pressure, nitric oxide levels, etc. as well as general change in the state of the heart such as, e.g., heart failure, ischemic state, etc. Also, by electrically stimulating at a low frequency and amplitude, the perturbation may have a small effect on the battery life of an IMD.

Figure 6:
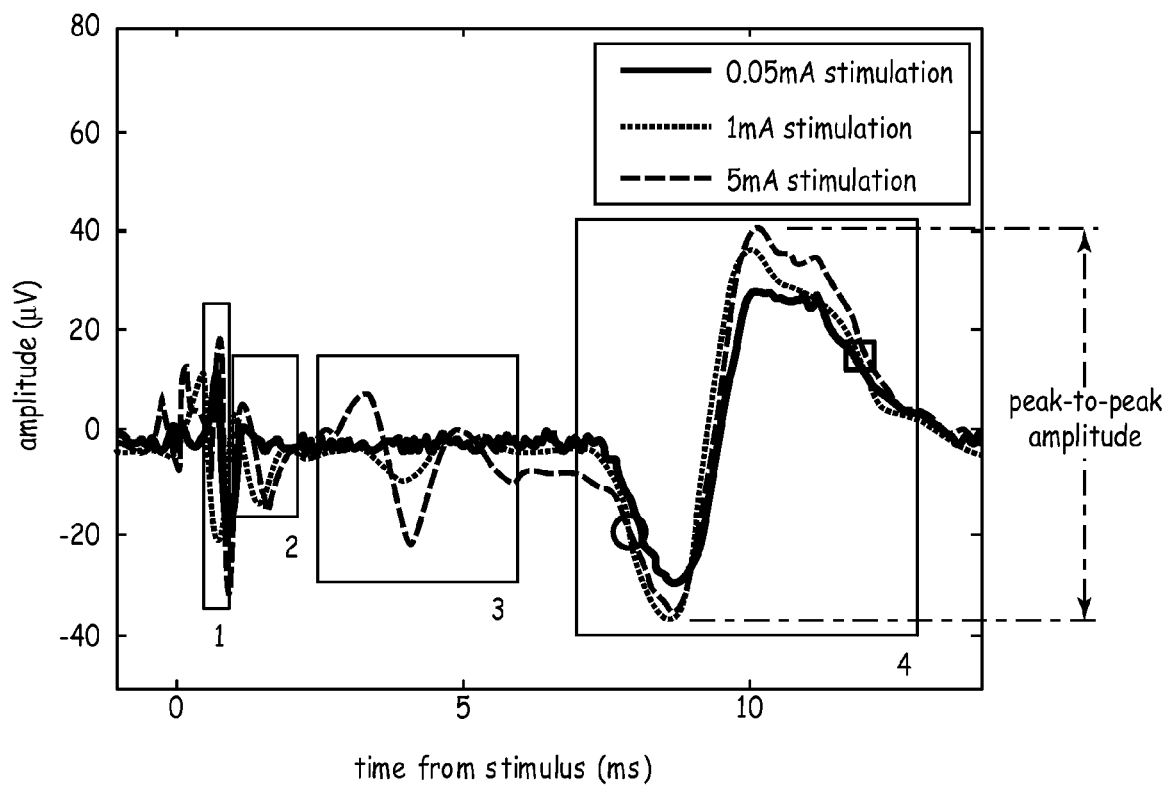
FIG. 6 is a graph displaying electrical stimulation at three different stimulation amplitudes which resulted in compound action potential data emanating from cardiac nerve tissue during an experimental study using pigs.

Referring to FIG. 6, exemplary CAPs, generated at the vagal trunk, is depicted. The latency, measured from the time that electrical stimuli is delivered, is 8.65 ms. Referring to box 4, the point of the highest slope at the beginning of the indirect component is indicated with a circle. The point of the highest slope at the end of the indirect component is indicated with a square. The dispersion, can be measured between the beginning and end of the indirect component, which is the time (i.e. 1.35 ms) between the circle and the square.

Further, therapy may be delivered to the heart based on the physiological parameters and/or general state of the heart determined by the assessment of the effect of the perturbation. For example, the heart could be influenced and titrated to a desired level by nerve stimulation to the vagus nerve or cardiac branch, sympathetic inhibition, pacing, ICD shocks, medication change, etc.

Figure 5:
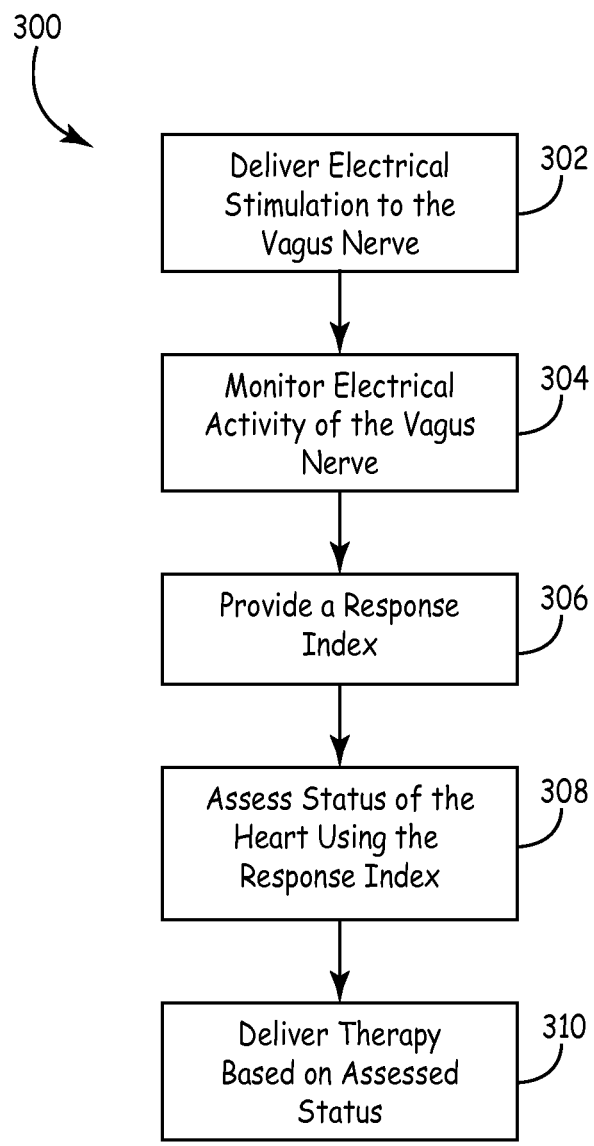
FIG. 5 is a flow chart depicting another exemplary method for use in treating a patient's heart by, e.g., perturbing a physiological system and assessing the effect of the perturbation on the patient's heart.

A flow chart depicting another exemplary method 300 for using in treating a patient's heart by, e.g., perturbing a physiological system and assessing the effect of the perturbation on the patient's heart, is depicted in FIG. 5. The method 300 includes perturbing at least one physiological system of the patient by delivering electrical stimulation to the patient's vagus nerve 302. The electrical stimulation may be similar to the electrical stimulation described herein with reference to process 102 of FIG. 3.

In at least one embodiment, the electrical stimulation delivered to the vagus nerve 302, or vagal stimulation, may include pulses (e.g., biphasic pulses) performed with a pulse width of about 30 microseconds to about 300 microseconds, a pulse amplitude range of about 0.05 milliamperes (mA) to about 5 mA, and a frequency of about 1 hertz (Hz) to about 50 Hz. Further, the stimulation trains may include about 10 to about 120 pulses. The individual pulses (e.g., at about 1 Hz) may include various amplitudes that may have been used to characterize a baseline situation (e.g., for a response index). Further, bursts of pulses (e.g., at about 50 Hz) with various amplitudes may be used. Still further, burst stimulation may be maintained for up to about 30 seconds. The vagal stimulation 302 may also be varied within the ranges of parameters recited herein in an effort to perturb the cardiovascular system in a plurality of ways such that a plurality of effects may be monitored and assessed using the response index.

During and/or after the delivery of the electrical stimulation of the vagus nerve 302 (i.e., the perturbation), the method 300 includes monitoring physiological parameters of the patient, which includes monitoring electrical activity of the patient's vagus nerve 304. The electrical activity of the patient's vagus nerve may include one or more signals and may be monitored (e.g., using one or more electrodes) from locations in or around the patient's vagus nerve. Such signals may include parasympathetic and/or sympathetic signals propagating along efferent and afferent nerve fibers. In at least one embodiment, the electrodes may be electrode cuffs that include at least three electrode contacts (e.g., each cuff being 15 millimeters (mm) long with the distance between each contact of about 4 mm). In one or more embodiments, an afferent signal to the brain can be amplified.

The monitored electrical activity of the patient's vagus nerve may be measured using the average reference method as outlined in L. Kornet et al., Average Reference Recording From The Vagal Nerve Reveals An Evoke Indirect Response, $4^{th}$ International IEEE EMBS Conference On Neural Engineering, Antayla, Turkey (Apr. 29-May 2, 2009), incorporated by reference in its entirety. The average reference method determines a reference signal by averaging of all sensed signals over a predetermined period of time (e.g. 20 kHz). In the average reference method, the average of all recorded channels from one cuff is subtracted from each channel of the cuff separately. For example, if the cuff includes three electrodes, then the average of the signals recorded at each of the three electrodes will be subtracted from each signal recorded at each electrode of the cuff. Using this average reference method, disturbances coming from signals in other electrodes or cuffs may be avoided. In addition, the average reference method may allow for detection of very fast signals (for example, indirect component(s)), which with a bipolar configuration (e.g., using another reference electrode) may not be capable of detecting. Thus, individual peaks of amplitude over time from a CAP, which is the response to perturbation of a single pulse, will be better distinguished with the average reference method as compared to a bipolar method. Signals with a certain velocity or higher can not be distinguished with the bipolar method but can still be detected with the average reference method.

In at least one embodiment, the electrical activity effect may be found in the afferent electrical activity of the patient's vagus nerve. As such, process 304 may include various processes to filter the electrical activity to specifically monitor the afferent electrical activity of the vagus nerve. More details of methods and devices for use in processing nerve signal activity and delivering therapy are described, e.g., in U.S. patent application Ser. No. 12/770,227 filed 29 Apr. 2010 which was converted to U.S. Prov. Pat. App. No. 61/397,703 on 30 Jul. 2010 entitled "NERVE SIGNAL DIFFERENTIATION" to Zhou et al. and U.S. patent application Ser. No. 12/770,275 filed 29 Apr. 2010 which was converted to U.S.

Prov. Pat. App. No. 61/397,702 on 30 Jul. 2010 entitled "NERVE SIGNAL DIFFERENTIATION IN CARDIAC THERAPY" to Zhou et al., each of which are incorporated herein by reference in their entirety. In at least another embodiment, the electrical activity effect may be found in the efferent electrical activity of the patient's vagus nerve (e.g., the perturbation may affect the heart negligibly but the brain may still react by sending nerve signals).

The method 300 further includes providing a response index that includes data representative of electrical activity effect of the vagus nerve as caused by one or more perturbations to the vagus nerve (e.g., electrical stimulation of the vagus nerve). The data representative of electrical activity effect of the vagus nerve may include data representative of an expected baseline effect on the heart caused by the perturbation to the at least one physiological system. For example, at least one expected effect on the heart (e.g., the indirect response) caused by a perturbation is described further herein with respect to FIG. 1.

Further, for example, the expected electrical activity may be an expected latency between a perturbation of the at least one physiological system (e.g., electrical stimulation of the vagus nerve) and electrical activity of the vagus nerve associated with the heart and/or an expected relationship between a perturbation of the at least one physiological system and electrical activity of the vagus nerve associated with the heart. Further, the response index may include data based on activity levels of the patient, e.g., such that different data corresponding to different activity levels of the patient may used to assess the patient's heart depending on the activity level of the patient.

The method 300 further includes assessing a status of the patient's heart 308 by comparing the response index with the physiological parameters monitored after perturbing the at least one physiological system of the patient and delivering therapy to the patient based on the assessed status of the patient's heart 310.

For example, the method 300 may compare the monitored electrical activity of the patient's vagus nerve to a baseline value (or range of baseline values) indicative of healthy or unhealthy functionality of the organ (e.g. heart etc.) or organ/nerve system. If the monitored electrical activity is not close to the baseline value (or within a range of baseline values), then the method 300 may assess 308 that the organ or organ/nerve system may be either healthy or unhealthy.

Further, for example, the method 300 may compare the monitored electrical activity of the patient's vagus nerve to a marker value (or range of marker values) indicative of a disease or condition of the organ or organ/nerve system. If the monitored electrical activity is close to the marker value (or within a range of marker values), then the method 300 may assess 308 that the organ or organ/nerve system may have or may be affected by a disease or condition.

After the assessment 308, the method 300 may deliver therapy to the patient (e.g., the patient's organ or organ/nerve system) based on the assessed status of the heart 310. For example, the method 100 may deliver pacing therapy to increase a slow heart rate, vagal stimulation to decrease a fast heart rate, etc.

One such marker or baseline with respect to the cardiovascular system was determined by perturbing (e.g., electrically stimulating at various parameters) the left vagus nerve while monitoring the electrical activity of the right vagus nerve and vice versa. Further, simultaneous recordings from the left and right vagus nerves were performed while perturbing the left vagus nerve. By using the average reference method described herein, the electrical activity (e.g., the compound action potentials) of the vagus nerve was recorded in response to the perturbation (e.g., the electrical stimulation) at consecutive electrode sites.

Referring to FIG. 6, graph 400 displays exemplary CAP data 401, generated in response to three different electrical stimuli amplitudes delivered to vagal nerve tissue of ten female Dutch Landrace pigs, described in greater detail below. Briefly, data 401 is a sample of data that generally represents average electrical activity over 120 monitored electrical activities of the vagus nerves for 10 pigs plotted in a graph 400 having an x-axis representative of time in milliseconds from the perturbation (e.g., the electrical stimulation of the vagus nerve) and a y-axis representative of the measured amplitude in microvolts ($\mu V$) of the electrical activity. Data 401 was obtained by monitoring afferent nerve tissue after delivering electrical stimuli, at time zero, from an electrode (e.g. cuff electrode, spiral electrode etc.) to the efferent nerve tissue. For example, the cuff electrode was directly coupled to the efferent nerve tissue of the cranial nerve 10 or nervus vagus trunk. Electrodes, such as a cuff electrode coupled to the targeted nerve tissue (e.g. vagal nerve such as the afferent nerve tissue, cranial nerve 10, nervus vagus trunk) to monitor a response to electrical stimuli. A cuff electrode can comprise various electrodes, which can include rings or virtual rings divided into segments. High velocity of a response from the electrical stimulation is monitored in the cuff electrode by dividing the distance of two rings within the cuff by the time that the signal passes across these two separate rings.

As depicted, three different electrical stimuli were delivered to afferent vagal nerve tissue or cranial nerve tissue X of a pig at 0.05 milliamperes (mA), 1 mA, and 5 mA, respectively, which generated, in response, a CAP for each stimuli. The average CAP (averaged over 120 responses in about 2 minutes) generated in response to the 0.05 mA electrical stimuli is shown as dotted lines, the CAP generated in response to the 1.0 mA electrical stimuli is shown as dashed lines, and the CAP generated in response to the 0.05 mA is a single bold line.

Within the data 401, four components were identified, as enumerated by each boxed component. Stimulation amplitude thresholds monitoring afferent nerve tissue after stimulating efferent tissue, were determined using electrical stimulation (i.e., the perturbation) having pulse widths of about 300 microseconds. Due to differences in threshold amplitude, the CAP at 0.05 mA only exhibits substantial peak to peak differences in components 1 and 4 whereas in boxes 2 and 3, the signal is substantially flat for stimuli amplitude at 0.05 mA. Therefore, the electrical stimuli for the 0.05 mA amplitude generates only components 1 and 4 since electrical stimuli (e.g. such as at 1 mA or 5 mA) greater than 0.05 mA is needed to generate components 2 and 3. Generally, to consider a component in response to a stimuli, at least two times the standard deviation of spontaneous activity must be present and it must occur after each pulse.

Standard deviation is a measurement of variability or diversity used in statistics and probability theory and it shows how much variation or "dispersion" exists compared to the average, mean, expected value or budgeted value. In contrast to the stimuli at 0.05 mA amplitude, electrical stimuli at 1 mA and 5 mA both generate CAPs in which each stimuli include components 1, 2, 3 and 4.

The first two components denoted in boxes 1, 2, respectively for each perturbation are fast (e.g., greater than 40 meters per second) and had a low stimulus amplitude threshold (e.g., of about 0.05 milliamps to about 0.4 milliamps). The first component is faster than the second component. Velocity of the response can be calculated by dividing distance between stimulus and measuring electrode by time between stimulus peak to peak of interest as shown in FIG. 6. Specifically, the first component had a threshold of about 0.13 miliamps and the second component had a threshold of about 0.39 milliamps. The third component, denoted in box 3, was the slowest of the components (e.g., less than 10 meters per second) and had a higher electrical stimulus threshold (e.g., of about 1.2 milliamps to about 2.9 milliamps).

The fourth component, also referred to as the indirect component or response, is associated with expected latency. The fourth component, outlined in box 4, is the monitored response from the afferent electrical activity as compared to the stimulus. The fourth component had a similar electrical stimuli threshold value to the second component (e.g., about 0.05 milliamps to about 0.5 milliamps) but a longer latency measured from the perturbation (e.g., the electrical stimulation of the vagus nerve). The fourth component therefore travels a longer pathway than the other components. In particular, the fourth component travels from the direction of the heart. Latency is measured from time zero until steepest part of the slope of the fourth component or peak 4, as encircled in FIG. 6. Dispersion of the indirect component is the time between the steepest slope at the beginning (denoted by the circle on FIG. 6) and the end of the indirect fourth component (denoted by the square on FIG. 6).

Thus, the timing/latency on the x-axis can be used for components 1 through 3; however, the timing/latency on the x-axis cannot be translated directly to a velocity of the fourth component using distance between electrodes. To estimate the velocity of the fourth component, the latency is divided by traveled distance. If it is assumed that the traveled distance from a stimulus electrode to the heart and back to the sensing electrode is about 0.4 m, then the velocity is about 0.4 m/0.01 s=40 m/s.

The timing/latency does not reflect that the fourth component is actually fast. The fourth component occurred with a small latency on all consecutive recording sites, showing that it had a high velocity within the electrode cuff (e.g., greater than 40 meters per second). The long latency between perturbation and recording as well as the high velocity within the cuff shows that this fourth component is not a direct response to the perturbation, but traveled a longer path before entering the cuff, and therefore, is an indirect response. In particular, high velocity within the cuff is the velocity measured by dividing distance between first and second electrode by time difference of the signal being sensed on the first ring and time that the signal is sensed on second ring.

The indirect response, i.e., the fourth component, occurs in both the left and right vagus nerve when stimulating (e.g., perturbing) at the cervical level and does not originate in the brainstem but appears to be generated from the neural network of the heart. In one or more other embodiments, efferent nerve tissue could be monitored after stimulating afferent tissue. The same or similar techniques described above could be used herein.

Further, a decreased heart rate appears to be related to an indirect response having a longer latency and decreased amplitude. For example, in one experiment, on average, latency increased by 9% from its previous value while heart rate decreased by 8%. Conversely, an increased heart rate appears to be related to an indirect response having a shorter latency. For example, in one experiment, on average, heart rate increased by about 60% whereas latency decreased by about 43%. There is little or no relationship between percentage change in latency and heart rate. As a result, the latency of the indirect response of the electrical activity of the vagus nerve in response to electrical stimulation (i.e., a perturbation) of the vagus nerve may be used as a marker or baseline indicative of the state of the cardiovascular system.

Further, as described, the threshold value of the perturbation may also be used to analyze and/or identify various components. For example, the third component had a much higher threshold than the other three components, and therefore, may be identified using this threshold value (e.g., the perturbation could be delivered both below the threshold and above the threshold and a comparison between the two monitored effect signals could yield the third component).

Figure 7:
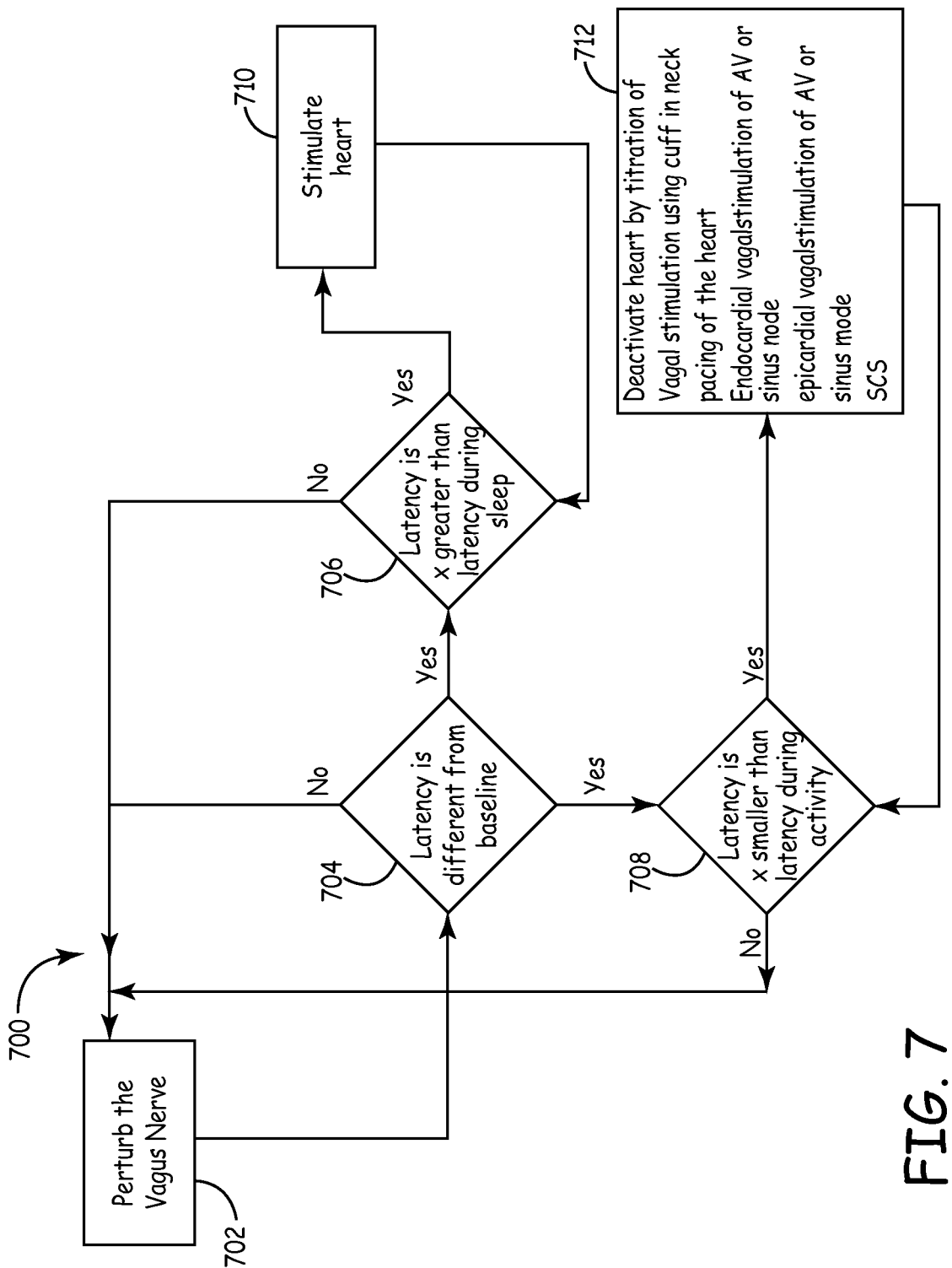
FIG. 7 is a flow chart depicting still another exemplary method for use in treating a patient's heart.
Figure 8A:
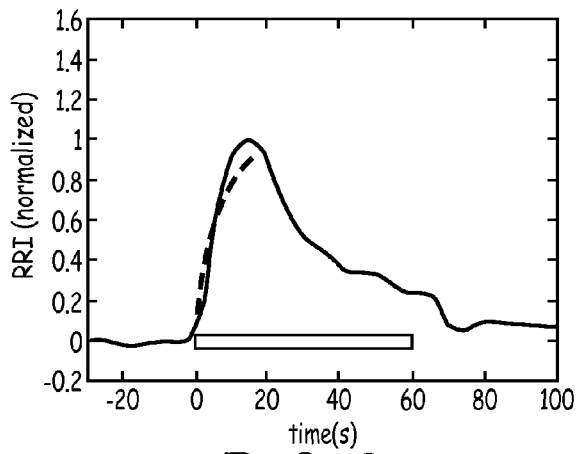
FIG. 8 shows multiple graphs displaying cardiovascular effect data as caused by a perturbation.
Figure 8B:
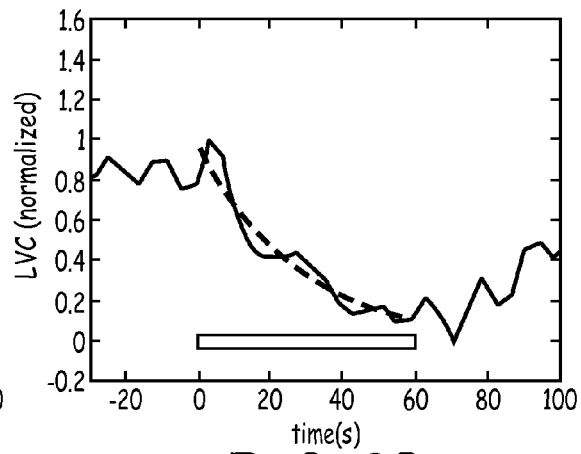
Figure 8C:
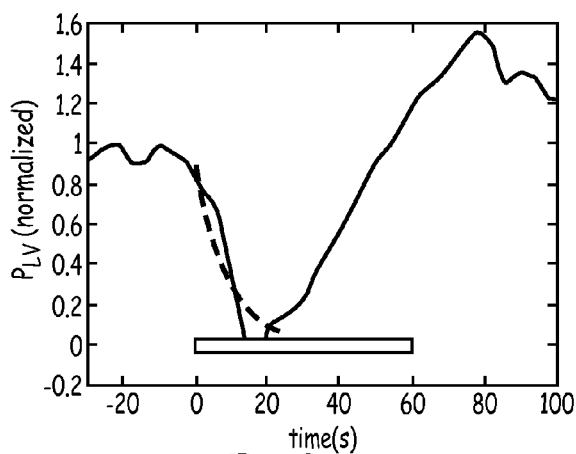
Figure 8D:
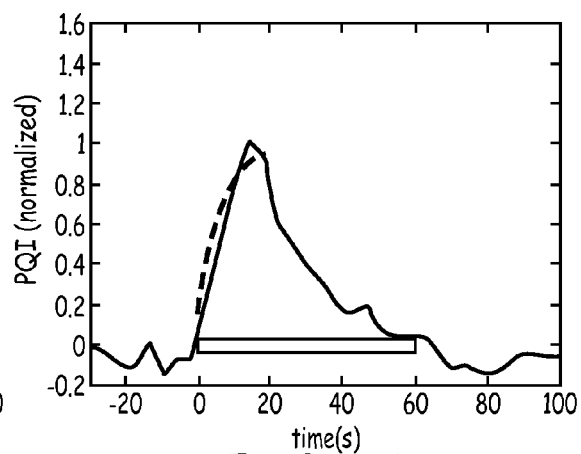
Figure 8E:
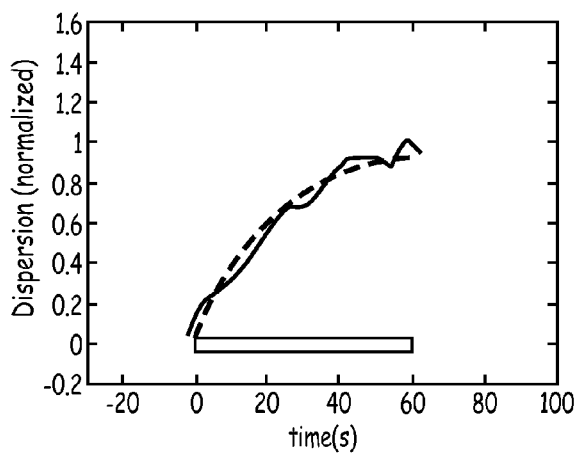
Figure 8F:
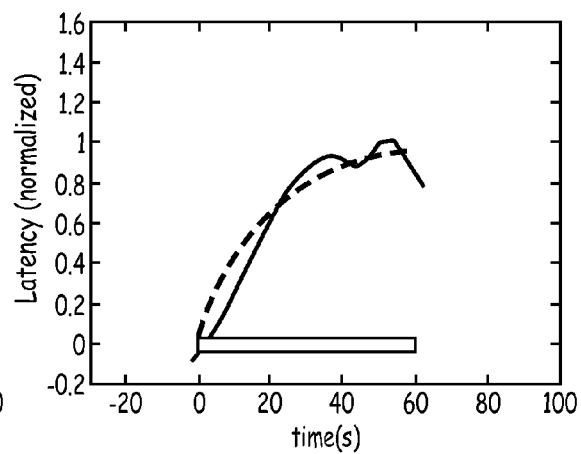

A flow chart of an exemplary method 700 for using in treating a patient's heart (e.g., based on the latency of the indirect response) is depicted in FIG. 7. The method 700 includes perturbing the vagus nerve of a patient 702, which may be similar to the perturbations 102, 302 described herein with reference to FIGS. 3 and 5. For example, the perturbation may be vagal nerve stimulation.

Although not shown, after and/or during the perturbation 702, the method 700 may include monitoring the physiological parameters of the patient. More specifically, the method 700 may include monitoring the electrical activity of the patient's vagus nerve for the indirect response as described above with reference to FIG. 6.

The latency of the monitored electrical activity, i.e., the time difference between the perturbation 702 and the monitored electrical activity, may be compared to baseline data for the indirect response included in a response index at block 704. If the monitored latency is no different than the baseline (e.g., similar to or about the same as the indirect response), then the method 700 may determine that no therapy is necessary (e.g., because monitored latency indicates that the heart is healthy). In one or more embodiments, the computer instructions executed by the microprocessor of the IMD 10 continues to monitor physiological parameters.

If the monitored latency is different than the baseline (e.g., for the indirect response), then the method 700 may determine if the latency is significantly greater than a first selected value representative of the latency within the response index 706. In another embodiment, If the monitored latency is different than the baseline (e.g., for the indirect response), then the method 700 may determine if the latency is significantly greater than a first selected value representative of the "latency during sleep" within the response index 706. Latency is determined multiple times during a recording for different states (e.g. one state can be a healthy condition while another state can be an unhealthy condition), p<0.05 using a t-test or non-parametric test. In one or more embodiments, two standard deviations away from the expected range for a particular patient can cause delivery of electrical stimuli to an afferent nerve. If the monitored latency is significantly greater than the first selected value, then the method 700 may determine to stimulate the heart using at least one selected therapy 710 (e.g., pacing, medication, etc.) to, e.g., increase the heart rate of the patient.

If the monitored indirect component(s), depicted by latency, and/or dispersion, is different than the baseline for that particular indirect component, then the method 700 may also determine if a parameter of the indirect component(s) (e.g. latency, dispersion) is significantly different. Latency or dispersion is determined multiple times during a recording at two states, p<0.05 using a t-test or non parametric test. For example, stimulation can be delivered 300 times each heart cycle, which, in turn, allows CAPs to be recorded or stored into memory. Significantly greater means that the resultant CAPS, which can be averaged, can then be compared to baseline data to determine whether a healthy or unhealthy condition exists. Significantly greater can mean that the monitored indirect response (i.e. latency, dispersion of the indirect component etc.) are two standard deviations away from the baseline.

Significantly less can be defined by an outlier compared to a second selected value representative of the "indirect component during activity" within the response index 708. If the monitored indirect component is significantly less than the second selected value, then the method 700 may determine to deactivate the heart using at least one selected therapy 712 (e.g., vagal stimulation, pacing, endocardial or epicardial vagal stimulation of AV node or sinus node, spinal cord stimulation, etc.) to, e.g., decrease the heart rate of the patient.

Each of the activation therapy 710 and the deactivation therapy 712 may include adjusting, or titrating, the therapy to achieve an optimal indirect component(s), and therefore, attempt to achieve an optimal heart rate. For example, if the method 700 determines that the indirect component (as described by latency and/or dispersion etc. is significantly greater than the first selected value 706, delivers pacing therapy 710 to, e.g., increase the heart rate, and the latency is still significantly greater than the first selected value, the method 700 may increase the amount of pacing therapy 710 until the latency is not significantly greater than the first selected value. Conversely, if the pacing therapy 710 has decreased the latency to significantly less than the first selected value, then the method 700 may decrease the amount of pacing therapy 710 until the latency is within an acceptable range. Likewise, the deactivation therapy 712 may be adjusted in similar ways. For example, the deactivation therapy 712 may be increased if the latency is still significantly less than the second selected value. Further, for example, if the deactivation therapy 712 has increased the latency to significantly greater than the second selected value, then the method 700 may decrease the amount of deactivation therapy 712 until the latency is within an acceptable range.

Although shown as a continuous loop, method 700 may occur either periodically, e.g., once a day, once an hour, once a minute, etc. depending on, e.g., the level of care required for the patient. The rate of change of the physiological parameters may be monitored and assessed after perturbing an organ such as the heart (e.g., through electrical nerve stimulation, etc.). Multiple graphs displaying cardiovascular effect data, due to perturbation, generated from a study using pigs are shown in FIG. 8A-8F.

It was determined, through experimental data, that the rate of change of the indirect component described or depicted by an expected latency and/or dispersion, during vagal nerve stimulation (VNS), correlates with cardiovascular parameters such as the rate of change of R-R interval (RRI), left ventricular pressure ($P_{LV}$), left ventricular contractility (LVC) and P-Q interval (PQI). The indirect component also changes with these same cardiovascular parameters when heart frequency is kept generally constant by atrial pacing. The relationship between the indirect component of a CAP to one or more cardiovascular parameters can provide a new clinical tool for assessing the state or status of an organ (etc. heart etc.); which, in turn, may assist in diagnosing and/or treating a cardiac condition or other conditions.

In each of the FIG. 8 graphs, the X-axis represents time (e.g., in seconds) and the Y-axis represents the particular cardiovascular parameter being measured. Further, the perturbation (e.g., vagal stimulation, vagal electrical stimulation etc.) is delivered at time 0. As shown, R-R interval (RRI) is plotted in Graph A, left ventricular contractility (LVC) is plotted in Graph B, pressure of left ventricle ($P_{LV}$) is plotted in Graph C, P-Q interval (PQI) is plotted in Graph D, dispersion (of the indirect component described herein) is plotted in Graph E, and latency (of the indirect component described herein) is plotted in Graph F.

Referring to Graph A of FIG. 8, the time constant between the initial rise of the R-R interval to the peak of the R-R interval may be used as effect data (e.g., for use in the response index). Using this effect data, a patient's heart may be perturbed and the time constant between the initial rise of the R-R interval to the peak of the R-R interval may be monitored and compared to the effect data. For example, if the presently-monitored time constant is different than the baseline data indicates as being healthy, then it may be indicative of a cardiac condition (e.g., tissue damage). Baseline data may be recorded in the same individual when it was healthy or be generated by the average of values in a database obtained in healthy individuals.

The data depicted in Graphs B-F of FIG. 8 may be used in a similar fashion to the data depicted in Graph A. In Graph B, the time constant between the peak of the LVC to the baseline value of the LVC may be used as effect data. In Graph C, the time constant between the peak of the $P_{LV}$ to the baseline value of the $P_{LV}$ may be used as effect data. In Graph D, the time constant between the initial rise of the P-Q interval to the peak of the P-Q interval may be used as effect data. In Graph E, the time constant between the initial rise of the dispersion (of the indirect component) to the peak of the dispersion may be used as effect data. In Graph F, the time constant between the initial rise of the latency (of the indirect component) to the peak of the latency may be used as effect data. Further, although only the time constants of the rises and declines of these cardiovascular parameters are described herein as effect data, various other statistical measures of these cardiovascular parameter (as well as others) may be used as effect data with the methods and devices described herein.

As shown in FIG. 8, each of the cardiovascular parameters was normalized between 0 and 1 with their initial value set at zero and the first peak value set at 1 during burst stimulation. Further, outliers were removed and linear interpolation was used to increase the sampling frequency to 1 hertz and to reduce estimator bias. Outliers can be identified from data by using methods described by William Mendenhall et al, Statistics for Engineering and Sciences ($4^{th}$ ed. 1987), incorporated by reference in its entirety. Still further, in some data recordings, the effect data reached a peak during stimulation and decreased again during stimulation (FIG. 8A-F). The initial rise or decline was solely used for correlation analysis. By solely using the initial rise (FIG. 8) for correlation analysis, the remaining data reflects the direct influence of the vagal nerve. In other embodiments, the initial decline (FIG. 8) can be solely used for correlation analyses, the remaining data reflects the direct influence of the vagal nerve.

Figure 9:
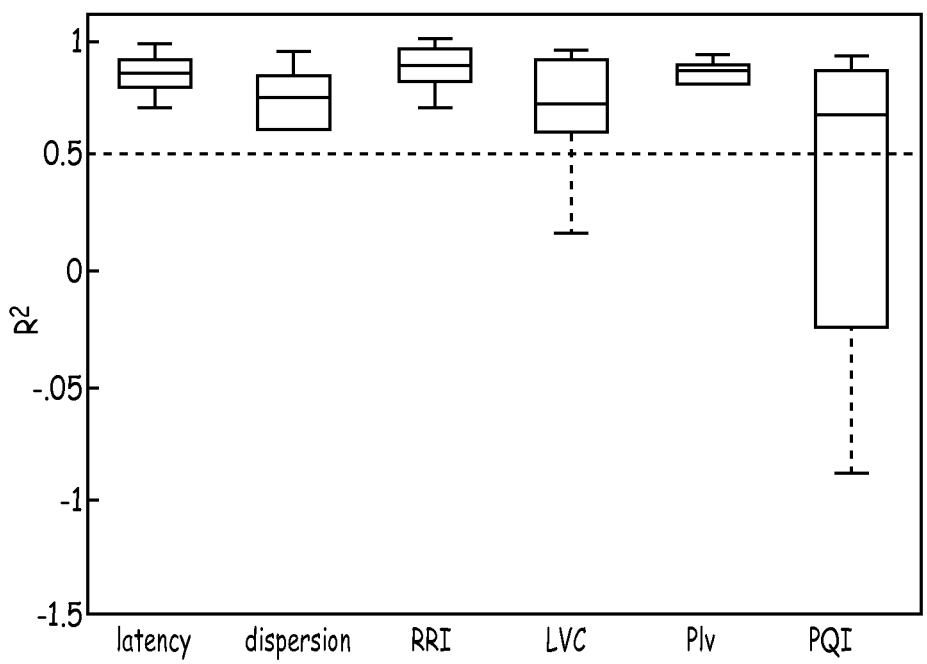
FIG. 9 shows multiple graphs displaying values of $R^2$ to fit to latency, dispersion, RRI, LVC, $P_{LV}$ and PQI.
Figure 10A:
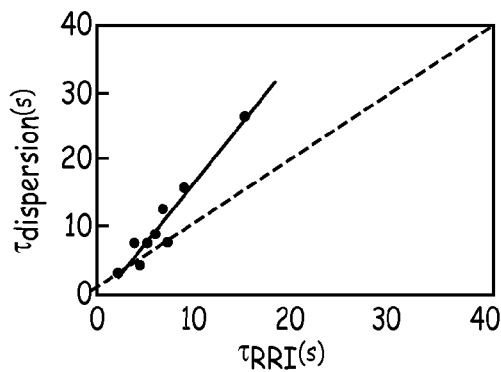
FIG. 10 shows multiple graphs displaying time constant data as caused by a perturbation.
Figure 10B:
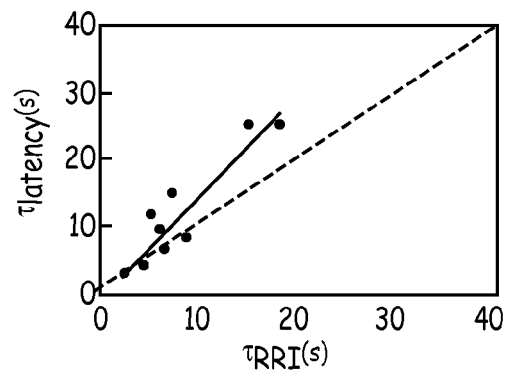
Figure 10C:
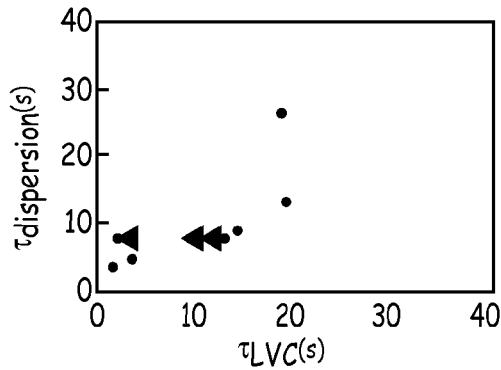
Figure 10D:
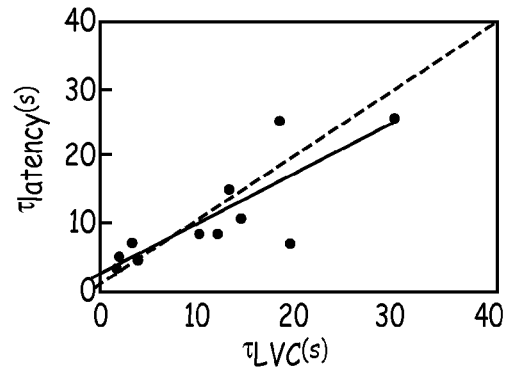
Figure 10E:
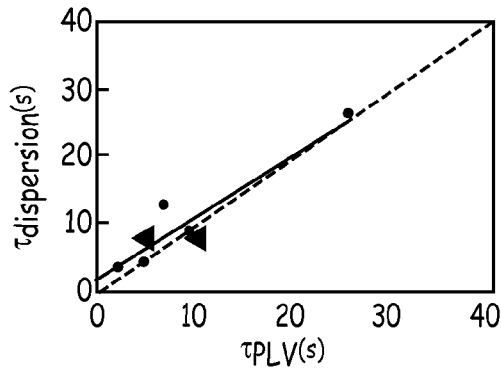
Figure 10F:
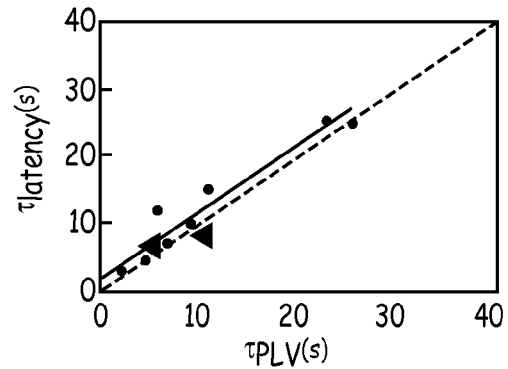
Figure 10G:
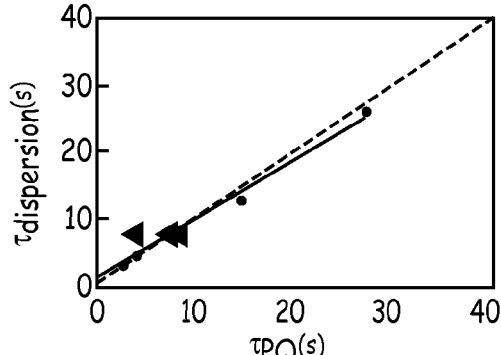
Figure 10H:
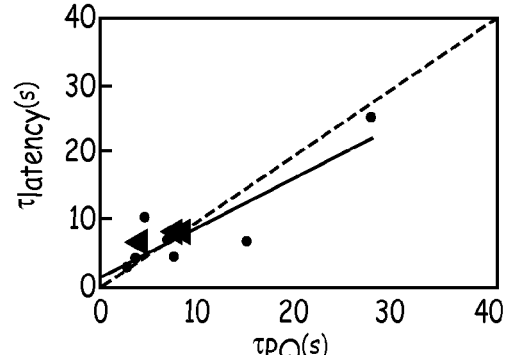

An exponential first order model, shown by dashed lines in FIG. 8, was fitted to the normalized parameters (e.g. R-R, LVC, Ply, PQI, dispersion or latency etc). The normalized parameters are referred to as y(t). The exponential first order was described by the parameter τ:

$$y(t) = 1 - e^{-\frac{1}{\tau}t}$$

for increasing parameters y,

Time constant τ describes the rate of change. In general, if a change is faster, τ is smaller. The Levenberg-Marquardt method was used for nonlinear least-squares optimization. The ability of the model to fit well or the goodness-of-fit of the model was evaluated by determining the coefficient of determination, which describes the variance between xi and yi accounted for:

$$R^2 = 1 - \frac{\sum_i (x_i - y_i)^2}{\sum_i (x_i - \bar{x})^2}$$

where $x_i$ is the original data, $\bar{x}$ is the mean value of the original data and $y_i$ is the fitted model. The model, which relied on data presented, for example in FIG. 9, was included in the analysis only if $R^2$ was 0.5 or higher. Experimental data for FIG. 9 is further discussed below.

Parameters such as latency, dispersion, RRI, $P_{LV}$, LVC and PQI were tested for normality using a Shapiro-Wilk test. Statistical significance of the effect of VNS on normally distributed parameters was tested with a one sample t-test. Effects on parameters such as latency, dispersion, RRI, $P_{LV}$, LVC and PQI that were not normally distributed were tested with a Wilcoxon test. Statistical significance of the results was tested at the 0.05-level using the statistical analysis package referred to as Statistical Package for the Social Sciences (SPSS). Linear regression analysis was used to assess the relationship between the indirect component, as expressed by latency and/or dispersion, and the cardiac parameters, by analyzing the correlation between their respective τ's. These τ's can be obtained from fitting as shown in FIG. 8. Significant linear correlation between the τ's of dispersion and latency with RRI, LVC, Ply, and PQi is summarized in Table 1. Significant linear correlation is determined using the least squares method, as presented on pages 302-310, by Altman, Practical Statistics for Medical Research). Linear regression can be performed on observed values of Y on X to derive a straight line that gives a "fitted" estimated value of Y for any variable of the parameter X. The general equation of a regression line is Y=a+bX. Here, b is the slope of the regression line and a is called the intercept. A will have no practical meaning. The slope assists in determining if there is a relationship between the parameters Y and X. A confidence interval of the slope and test the hypothesis of a zero slope with a p>0.95, that is of no relationship between X and Y. Assumptions made using linear regression are that: (1) values Y have a normal distribution, (2) variability is equal for Y and X, and (3) the relation ship between X and y is linear. The least squares method produces the line (i.e. relation between two parameters) that minimizes the sum of the squares of the residuals, and so it also minimizes the variance of the residuals, which is just the sum of squares divided by the number of observations minus two. This variance known as the residual variance, is a measure of the "goodness-of-fit" of the line and is defined as R and should be greater than 0.5. In case R=1, Y and X data are the same.

The slope of the linear regression line was significantly different from zero as indicated by a p value smaller than 0.05.

TABLE 1

Pearson's correlation coefficients between time constants

|  | $T_{dispersion}$ | $T_{latency}$ |
|---|---|---|
| $T_{RRI}$ | r = 0.955<br>P = 0.000 *<br>n = 9 | r = 0.927<br>P = 0.000 *<br>N = 10 |
| $T_{LVC}$ | r = 0.730<br>P = 0.063 | r = 0.815<br>P = 0.014 * |

TABLE 1-continued

Pearson's correlation coefficients between time constants

|  | $T_{dispersion}$ | $T_{latency}$ |
|---|---|---|
| $T_{Plv}$ | n = 7<br>r = 0.930<br>P = 0.001 *<br>n = 8 | N = 8<br>r = 0.960<br>P = 0.000 *<br>N = 9 |
| $T_{PQI}$ | r = 0.979<br>P = 0.001 *<br>n = 6 | r = 0.881<br>P = 0.020 *<br>N = 6 |

The asterisk indicates a significant relationship of p<0.05 between the parameter on x and y-axis by assessing the confidence interval of the slope of the linear regression line, which should be significantly different from zero.

Response indices can be applied to the cardiovascular parameters depicted in FIG. 8. A response index can be data representative of such cardiovascular effects shown in FIG. 8 as caused by one or more perturbations to the cardiovascular system. Additionally, such cardiovascular parameters and their time constants may be monitored after perturbation and may be assessed using the response index. For example, the time constants and/or exponential first order model/functions may be part of the response index to be used in one or more assessments.

Moreover, correlations may exist between two or more of the monitored parameters and such correlations may be a response index. For example, a high linear correlation (R higher than 0.5, and/or 0.5 to 1.0) may exist between latency of the fourth component and the RRI and between the latency of the fourth component and the PQI. Further, for example, the dispersion of the indirect component may also be correlated with the RRI but may not correlate with the PQI. Additionally, dispersion of the fourth component may be correlated with the LVC.

During bursts of electrical stimuli, blood pressure and left ventricular contractility decreased, while R-R interval and PQ-time increased. Table 2, presented below, summarizes the effects of vagal burst stimulation. Experimental data in Table 2 was obtained through electrical stimulation delivered to the vagus nerve through pulses performed with a pulse width of about 300 microseconds, a pulse amplitude range of about 10 milliamps (mA, and a frequency of about 50 Hz. For RRI, the effect percentage is 18±16 with a p value that is 0.03. For PQI, the effect percentage is 23±30 with a p value that is 0.08. For LVC, the effect percentage is −10±7 with a p value that is 0.013. For PLV, the effect percentage is −11±7 with a p value that is 0.004.

TABLE 2

Summary of the effects of vagal burst stimulation
(300 microseconds, 10 mA, 50 Hz).

| Parameter | Effect (%) |
|---|---|
| RRI | 18 ± 16 (p = 0.03) |
| PQI | 23 ± 30 (p = 0.08) |
| LVC | −10 ± 7 (p = 0.013) |
| PLV | −11 ± 7 (p = 0.004) |

The indirect component, found in each CAP, exhibited a high velocity (more than 40 m/s) and a low stimulation threshold (components (0.16±0.14 mA) therefore, each indirect component emanates not directly from the stimulus but travels a longer path and is carried by the fibers of the vagal nerve. Specifically, the indirect component of the evoked CAP finds its origin in the 'little brain on the heart', which is comprised of parasympathetic neurons, sympathetic neurons and interconnecting neurons. The 'little brain of the heart' transduces neural inputs and coordinates cardiac electrical and mechanical parameters. Detailed information concerning the signaling pathways and coordination within the cardiac neuronal hierarchy is scarce. Interactions between the sympathetic and parasympathetic neurons occur at multiple sites, including the intrinsic cardiac network.

An initial effect was observed on both the cardiovascular parameters and the indirect component of electrical vagal nerve stimulation (VNS) at certain stimulation levels. The time constants of several cardiovascular parameters were compared during VNS to parameters describing the indirect component of the CAPs or their time constants. First or second order models were used to describe the effects of VNS on the heart The data generated for FIG. 8 was based on experiments that were performed in ten female Dutch Landrace pigs in which the cervical vagal nerve was electrically stimulated with bursts of electrical stimuli. Each pig was premedicated with 0.5 mg/kg Morphine IM 20 minutes before induction. Zoletil (Telazol), 3 mg/kg, IM and xylazine 0.5 mg/kg, IM were administered. Isoflurane was maintained once the pig was intubated, the IV line was placed and the paws were shaved for fitting ECG electrodes. The pig was anesthetized with a combination of isoflurane (0-1.5%) and fentanyl (6-10 μg/kg/hr).

The left vagal nerve was dissected free from the surrounding tissue and two custom-made self-coiling cuff electrode configurations were placed for recording and stimulation respectively. Each cuff was 15 mm long and had three circular platinum/iridium (Pt/Ir) electrode contacts with an interelectrode distance of 4 mm. The cuff was made in various diameters (2, 3.5 and 5 mm), to ensure a proper fit around the nerve. ECG recordings were made with the contact electrodes. The left ventricular pressure ($P_{LV}$) was recorded with a Millar catheter.

ENG signals, defined as signals sensed on the nerve, were amplified by a TMSi Refa amplifier commercially available from TMS international, located in Oldenzaal, The Netherlands. ECG and blood pressure recordings were amplified with a TMSi Porti amplifier. ENG was sampled at a frequency of 20 kHz and the ECG and $P_{LV}$ were sampled at 2048 Hz. Data was stored on a computer using PortiLab2 software commercially available from TMS international, located in Oldenzaal, The Netherlands.

The vagal nerve was stimulated using biphasic pulses generated by a custom-made stimulator. VNS was performed with a pulse width of 300 μs, a pulse amplitude range of 0.1-5 mA, and a stimulation frequency range of 10-50 Hz. Bursts of pulses with various amplitudes were used to influence heart rate. VNS was maintained for up to 60 seconds. Various stimulation settings were tested, until an effect on the RR interval was found. For each pig, the recording in which the RR interval increased most was selected. In the selected recordings, a sinus rhythm was maintained throughout the experiment.

In three pigs, VNS at the settings at which RR interval increased most was repeated while pacing the heart with pacing leads placed in the right atrium. Through pacing, heart rate was kept substantially constant at a rate of at least ten percent above baseline levels to assess the change in cardiovascular parameters and the CAPs, independently of heart rate.

Offline signal analysis was performed in Matlab R2007a commercially available from The Mathworks Inc. P, Q and R-tops of the ECG were automatically detected and confirmed by visual inspection. R-R and P-Q intervals were determined. P-Q interval (PQI) length was normalized on heart cycle duration by dividing PQI by R-R interval (RRI). Left ventricular contractility (LVC) was assessed using maximum values of the gradient of $P_{LV}$ recordings:

$$\left(\frac{dP_{LV}}{dt}\right)_{max}.$$

The course of left ventricular pressure ($P_{LV}$) was determined as the values of the peaks of each cycle of the pressure recordings over time. Variations in the cardiac parameters due to respiration were reduced by using non-overlapping four second averaging windows. Stimulation artifacts were detected in the ENG. After noise was reduced by applying a low pass filter with a cutoff frequency of 500 Hz, latency of the indirect component was determined using the point of the highest initial slope (e.g. provide example and preferably tie it to a figure.) of the indirect component depicted in FIG. 6. The time between stimulus artifact and the point of the highest slope is referred to as. latency of the indirect component. Dispersion of the indirect component is the time between the highest slopes at beginning and end of the indirect component.

In two out of ten pigs a complete atrioventricular block (AV block) occurred during VNS; however, it was determined that by adjusting stimulation parameters, AV-block could be avoided. AV-Block is a condition in which faulty transmission of the impulses that control the heartbeat results in a lack of coordination in the contraction of the atria and ventricles of the heart. There are three types of AV block. First degree AV block occurs when the PR interval is greater than 0.20 sec. Second degree AV block Type 1, (also referred to as Mobitz 1, Wenckebach), involves progressive prolongation of PR interval with dropped beats (the PR interval gets longer and longer; finally one beat drops). Type 2 AV block (also referred to as Mobitz 2, Hay) occurs when the PR interval remains unchanged prior to the P wave which suddenly fails to conduct to the ventricles. Third degree AV block, also referred to as complete heart block, occurs when the impulse generated in the SA node in the atrium does not propagate to the ventricles.

Latency increased significantly compared to baseline during VNS by 9.4±5.2% (P=0.000, n=10). Dispersion also increased significantly (42±30%, P=0.002, n=10). LVC decreased significantly compared to baseline by a median 9% (P=0.005, n=10). RRI increased significantly by a median 18% (P=0.005, n=10). PQI increased significantly by 36±40% (P=0.013, n=9). $P_{LV}$ decreased significantly by 11±13% (P=0.024, n=10).

As expected, the course of cardiovascular parameters during burst stimulation varied between pigs and in some pigs a return toward baseline values occurred, as shown in Table 2 and FIG. 8. However, in all pigs, the initial rise or decline of the cardiac parameters was observed and was fitted with the exponential first order model. The value of $R^2$ was lower than 0.5 in one pig for the fit to $P_{LV}$, in four pigs for the fit to PQI, in two pigs for the fit to LVC and in one pig for the fit to dispersion. These eight fits were excluded from the analysis. A boxplot of the values for $R^2$ in all models is shown in FIG. 9.

A return towards baseline values during VNS was seen for LVC in one out of ten pigs, for $P_{LV}$ in two out of ten pigs and for PQI in four out of ten pigs. Most often it was seen in RRI, i.e. in five out of ten pigs. The time constant $\tau_{RRI}$ of this return in RRI was significantly larger than $\tau_{RRI}$ of the initial increase in RRI; 6.4±2.6 s and 15.7±6.9 s respectively (P=0.03, n=5).

Referring to FIG. 10, time constants ($\tau$) such as $\tau_{latency}$ was assessed as possessing a significant linear correlation with $\tau_{RRI}$, $\tau_{LVC}$, $\tau_{Plv}$ and $\tau_{PQI}$ which is summarized in Table 1. The $\tau_{dispersion}$ also significantly correlates with $\tau_{RRI}$, $\tau_{Plv}$ and $\tau_{PQI}$, but not with $\tau_{LVC}$ as shown in table 1. The correlation coefficients differed from 1, showing that time constants are correlated, but not identical.

In three pigs VNS was repeated while atrial pacing of the heart was performed at a constant rate above baseline heart frequency. Referring to FIG. 10, the values of $\tau$ are similar to those found without pacing.

In a previous experiment, an indirect response to cervical vagal nerve stimulation was determined to exist. Based on data obtained, the velocity of the afferent limb and stimulation of the efferent limb both matched cardiac fiber types. It appears that the response came from cardiac fibers and originated in the neural network on the heart.

The latency and dispersion of the indirect component during VNS were related to the cardiac parameters RRI, $P_{LV}$, LVC and PQI. Latency, dispersion and these four cardiac parameters changed significantly during VNS.

Latency and dispersion were determined from the highest slope at the beginning and the end of the component. This method was chosen over the use of a set threshold, because it is less susceptible to noise and less variability will result from variations in amplitude and shape of the component. A first order exponential model was used to characterize the parameters during VNS. A relationship was found between most of the time constants of the exponential model. Time constants $\tau_{RRI}$, $\tau_{LVC}$, $\tau_{Plv}$ and $\tau_{PQI}$ were linearly correlated to $\tau_{latency}$. Time constants $\tau_{RRI}$, $\tau_{Plv}$ and $\tau_{PQI}$ were also linearly correlated to $\tau_{dispersion}$, $\tau_{LVC}$ was not.

After an initial increase in RRI during VNS, RRI decreased by more than ten percent of the peak effect towards baseline levels while VNS was continued in five out of nine pigs. The rate of change of this decrease was significantly lower than that of the initial rise, which supports a finding that the first increase is related to the parasympathetic system and that the second change involves the sympathetic system, since it is known that the effects of the sympathetic system starts with a delay. Additionally, the parasympathetic input is increased instantaneously by the direct stimulation of the vagal nerve, while the sympathetic reaction is a reflexive process. Therefore, it can be expected that the sympathetic effect takes place later in time, which supports inclusion of only the initial rise or decline of a cardiac parameter when analyzing its link to the parasympathetic system.

When the heart rate was kept relatively constant through atrial pacing, similar values compared to the unpaced condition were obtained for the estimated $\tau$ for latency, dispersion, PQI, LVC and $P_{LV}$. Experiments with atrial pacing were performed in three pigs indicating that the indirect component changes when cardiovascular parameters change, independent of heart frequency. The indirect component can be a useful marker of cardiovascular parameters that may not be assessed through monitoring heart rate. The indirect component is readily available from a nerve recording.

It is unlikely that changes in axon excitability caused the change in latency and dispersion of the indirect component, because myelinated fiber types are involved. Additionally, electrical stimulation was performed well above fiber excitation threshold and therefore variations in recruitment characteristics around fiber threshold were not involved. Latency may have increased due to an increase in relay time at the neural network of the heart. A greater variability in relay time could lead to a larger dispersion of the indirect component.

$$\left(\frac{dP_{LV}}{dt}\right)_{peak}$$

was used as a measure for left ventricular contractility. In an intact animal $$\left(\frac{dP_{LV}}{dt}\right)$$

is dependent on load and heart rate. It is therefore possible that changes in heart rate have influenced our estimation of left ventricular contractility. An alternative would be to use a pressure-volume curve to assess load-independent contractility, which would require a pressure-volume catheter.

In sum, the relationship between the indirect component of the vagal CAP and the cardiovascular system was assessed. During VNS the rate of change of the indirect component correlates with the rate of change of RRI, $P_{LV}$, LVC and PQI. The indirect component also changes with these cardiovascular parameters when heart frequency is kept constant by atrial pacing.

Figure 11:
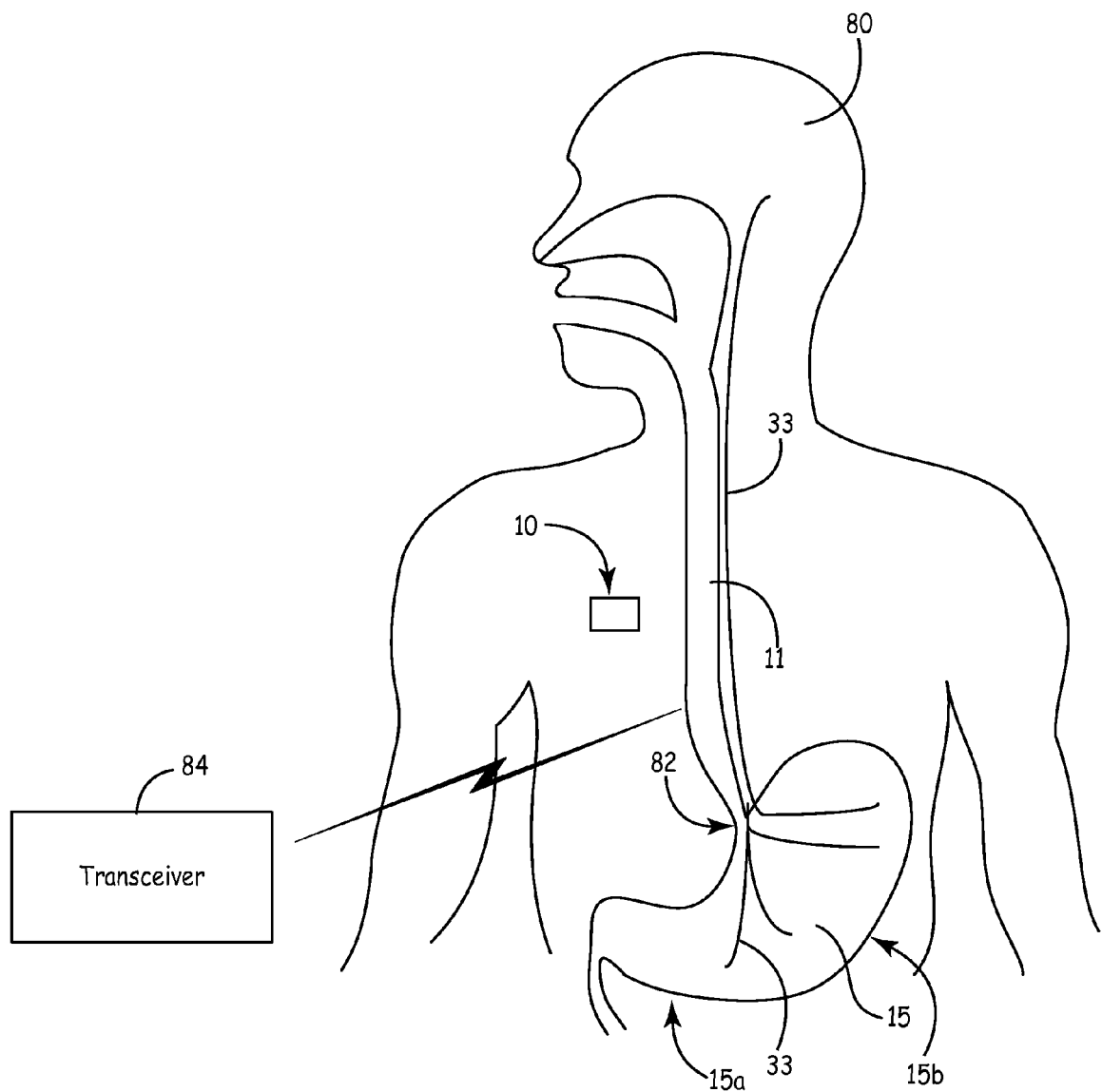
FIG. 11 is a schematic diagram illustrating an IMD connected to a gastrointestinal system of a patient.

FIG. 11 is a schematic diagram illustrating an IMD 10, in a patient 8, that controls consumption of food to reduce weight. IMD 10 can be configured as a combined cardioneuro device, as previously described, or as a separate ICD and neurostimulator. IMD 10 has a medical electrical lead 14 disposed near or coupled to stomach 15 and another medical electrical lead 16 coupled to or in close proximity to the vagal nerve or vagal nerve tissue 33. Vagal nerve 33 extends from stomach 15 past esophageal sphincter 22 i.e., where esophagus 11 meets stomach 15, into the brain. Medical electrical lead 16 can include one or more electrodes (e.g. ring and tip electrodes etc.) such as a bipolar lead.

In one or more embodiments, optimal placement of lead 14 can depend on a portion of the stomach 15 that is most likely to expand when food resides or begins to reside therein. For example, electrodes and/or sensor(s) at the distal potion of medical electrical lead 14 can be placed at bottom portion 15a of stomach, and/or side portions 15b of stomach 15 in order to sense expansion of stomach 15. Other means can be used for placement of sensors or devices to monitor food consumption are described in U.S. Pat. No. 7,299,091 issued Nov. 20, 2007 to Barrett et al, which is incorporated by reference in its entirety.

IMD 10 is capable of sensing whether a stomach of a patient has attained a predetermined level of nourishment (e.g. ¼ full, ½ full, ¾ full, full etc.). IMD 10, in turn, can sense through an electrode on medical electrical lead 16 the efferent electrical activity in response to the electrical stimulation of the afferent nerve. After sensing the efferent electrical activity, IMD 10 can continuously monitor and determine whether the efferent electrical response should be amplified to indicate that the stomach has achieved a certain level of nourishment (e.g. ¼ full, ½ full, ¾ full, full etc.).

To implement this method, IMD 10 is capable of delivering additional nerve stimulus or inhibition of nerve stimulus to an efferent nerve through lead 14 and/or 16. Furthermore, IMD 10 includes a sense amplifier. The sense amplifier can amplify the efferent nerve signal if a condition is met. For example, if the efferent signal does not meet a threshold level, then the efferent signal is amplified back to the brain.

The threshold level can be a predetermined level. For example, the threshold level can be customized to each patient through a trial and error process. Exemplary circuitry configuration for amplification of a signal may be seen with respect to U.S. Pat. Pub. No. 2009/0082691 A1 published Mar. 26, 2009, and assigned to the assignee of the present invention, the disclosure of which is incorporated by reference in its entirety herein. Thereafter, the brain signals the body to cause or trigger the release of a fullness hormone (e.g. peptide YY3-36 (PYY)) to stop eating. Release of PYY can reduce caloric intake up to one third of a patient's typical meal.

A transceiver 84 can optionally be used in wireless communication with IMD 10. In particular, IMD 10 can transmit data, such as indications of fullness, to transceiver 84 via inductive telemetry techniques known in the art. Transceiver 84 may include a coil antenna (not shown) to facilitate transmittal of data. Transeiver 84 may, for example, comprise a portable receiver that is carried by patient 8, e.g., a pager-like device that may be attached to a belt or carried within a pocket of patient 8 and includes a patch antenna that may be attached to the skin of patient.

Transeiver 84 may store the information received from IMD 10, and in some embodiments may process the information. Transceiver 84 may include a user interface, e.g., a keypad and display, and may display flow information received from IMD 10 to patient 8. The information stored within transceiver 84 may be downloaded by a clinician to a computing device and analyzed to diagnose the condition of patient 8. The computing device may process the information to provide the clinician with a variety of useful representations thereof.

All patents, patent documents, and references cited herein are incorporated in their entirety as if each were incorporated separately. The present disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed is:

1. A method for using an implantable medical device, the method comprising:
    delivering electrical stimuli to an afferent nerve associated with the selected organ;
    monitoring efferent electrical activity in an efferent nerve responsive to delivering electrical stimuli to the afferent nerve, wherein the monitored efferent electrical activity includes an indirect component of a compound action potential (CAP), wherein the indirect component is not in direct response to the delivered electrical stimuli; and
    assessing a status of the selected organ based upon the indirect component.

2. The method of claim 1, wherein assessing a status of the selected organ based upon the indirect component comprises assessing one of expected latency and dispersion of the indirect component.

3. The method of claim 2, wherein the expected latency is associated with a fourth peak in the CAP.

4. The method of claim 2, wherein an expected time constant of latency correlates to a time constant of an initial change in a cardiac parameter.

5. The method of claim 2, wherein the expected latency is represented by a time constant of latency.

6. The method of claim 2, wherein an expected time constant of dispersion correlates to a time constant of an initial change in a cardiac parameter.

7. The method of claim 1, wherein the electrical stimuli is burst pacing.

8. The method of claim 7, wherein the burst pacing treats a condition.

9. The method of claim 1, wherein the electrical stimuli is a single pulse.

10. The method of claim 9, wherein the single pulse provides data related to a status of a nerve-organ system.

11. The method of claim 10, wherein the single pulse does not provide treatment.

12. The method of claim 1, wherein the efferent electrical activity is associated with dispersion of a fourth component in a compound action potential.

13. The method of claim 12, wherein the dispersion forms multiple peaks in response to a single pulse of electrical stimuli.

14. The method of claim 13, wherein the dispersion is represented by a time constant of dispersion.

15. The method of claim 1, wherein the afferent electrical activity is associated with a burst pattern during a predetermined phase of a cardiac cycle.

16. The method of claim 1, wherein a status of the selected organ is not permanently affected by the delivered electrical stimuli.

17. A method for determining a fullness of a stomach using an implantable medical device, the method comprising:
    delivering electrical stimuli to an afferent nerve associated with the stomach;
    monitoring efferent electrical activity responsive to delivering electrical stimuli to the afferent nerve;
    assessing a status of the stomach in response to the monitored efferent electrical activity; and amplifying a signal to the vagal nerve to indicate the stomach is partially full.

18. The method of claim 17, wherein the electrical stimuli is burst pacing.

19. The method of claim 17, wherein the electrical stimuli is a single pulse.

20. The method of claim 19, wherein the single pulse provides data related to a status of the stomach.

\* \* \* \* \*